US012472096B2

(12) United States Patent
Jiang et al.

(10) Patent No.: US 12,472,096 B2
(45) Date of Patent: Nov. 18, 2025

(54) METHOD AND DEVICE FOR TREATING EYE DISEASE

(71) Applicant: Avisi Technologies, Inc., Philadelphia, PA (US)

(72) Inventors: Rui Jing Jiang, Lexington, MA (US); Brandon Wei-Hsiang Kao, Placentia, CA (US)

(73) Assignee: Avisi Technologies, Inc., Redwood City, CA (US)

( * ) Notice: Subject to any disclaimer, the term of this patent is extended or adjusted under 35 U.S.C. 154(b) by 673 days.

(21) Appl. No.: 17/423,419

(22) PCT Filed: Jan. 17, 2020

(86) PCT No.: PCT/US2020/014173
§ 371 (c)(1),
(2) Date: Jul. 15, 2021

(87) PCT Pub. No.: WO2020/150657
PCT Pub. Date: Jul. 23, 2020

(65) Prior Publication Data

US 2022/0125637 A1 Apr. 28, 2022

Related U.S. Application Data

(60) Provisional application No. 62/794,139, filed on Jan. 18, 2019.

(51) Int. Cl.

| | |
|---|---|
| ***A61F 9/007*** | (2006.01) |
| ***A61L 27/30*** | (2006.01) |
| ***A61L 27/34*** | (2006.01) |

(52) U.S. Cl.
CPC ........ *A61F 9/00781* (2013.01); *A61L 27/306* (2013.01); *A61L 27/34* (2013.01); *A61L 2430/16* (2013.01)

(58) Field of Classification Search
CPC .... A61F 9/00781; A61L 27/306; A61L 27/34; A61L 2430/16; A61L 27/10
See application file for complete search history.

(56) References Cited

U.S. PATENT DOCUMENTS

| | | | |
|---|---|---|---|
| 6,638,239 | B1 | 10/2003 | Bergheim et al. |
| 7,207,965 | B2 | 4/2007 | Simon |

(Continued)

FOREIGN PATENT DOCUMENTS

| | | | |
|---|---|---|---|
| CN | 108525023 | A | 9/2018 |
| JP | 2008-526371 | A | 7/2008 |

(Continued)

OTHER PUBLICATIONS

Notification of Reasons for Rejection, dated Oct. 31, 2023, for related Japanese Patent Application No. 2021-541251, with English translation attached.

(Continued)

*Primary Examiner* — Susan S Su
*Assistant Examiner* — Erin A Kim
(74) *Attorney, Agent, or Firm* — K&L Gates LLP

(57) ABSTRACT

Described herein are devices used to treat high intraocular pressure and glaucoma. An example device includes a plate comprising a first surface opposite a second surface. The first surface includes a series of fluid channels. The device also includes a first coating on the first surface and a second coating on the second surface. The device is configured to lower intraocular pressure by draining aqueous humor from an anterior chamber to subconjunctival space of a patient's eye.

20 Claims, 25 Drawing Sheets

(56) References Cited

U.S. PATENT DOCUMENTS

| | | | | |
|---|---|---|---|---|
| 8,246,569 | B1 | 8/2012 | Meng et al. | |
| 11,717,440 | B2 | 8/2023 | Kao et al. | |
| 2004/0254521 | A1 | 12/2004 | Simon | |
| 2005/0184004 | A1 | 8/2005 | Rodgers et al. | |
| 2005/0267398 | A1 | 12/2005 | Protopsaltis et al. | |
| 2006/0036207 | A1 | 2/2006 | Koonmen et al. | |
| 2008/0181930 | A1* | 7/2008 | Rodstrom | A61F 9/0017 514/469 |
| 2010/0249691 | A1* | 9/2010 | Van Der Mooren | A61F 9/00781 604/9 |
| 2010/0331975 | A1 | 12/2010 | Nissan et al. | |
| 2012/0273689 | A1 | 11/2012 | Sullivan et al. | |
| 2013/0150773 | A1* | 6/2013 | Nissan | A61F 9/00781 604/9 |
| 2015/0230983 | A1 | 8/2015 | Johnson | |
| 2016/0032230 | A1 | 2/2016 | Deutsch et al. | |
| 2016/0058615 | A1* | 3/2016 | Camras | A61F 9/00781 604/9 |
| 2017/0020730 | A1 | 1/2017 | Chew et al. | |
| 2023/0372152 | A1 | 11/2023 | Kao et al. | |
| 2024/0189145 | A1 | 6/2024 | Jiang et al. | |

FOREIGN PATENT DOCUMENTS

| | | | |
|---|---|---|---|
| JP | 2012-531274 | A | 12/2012 |
| JP | 2017-506139 | A | 3/2017 |
| WO | 0006223 | A1 | 7/1998 |
| WO | 2006/074391 | A2 | 7/2006 |
| WO | 2009/085548 | A2 | 7/2009 |
| WO | 2010/026557 | A2 | 3/2010 |
| WO | 2010/111528 | A2 | 9/2010 |
| WO | 2010/151779 | A1 | 12/2010 |
| WO | 2015/126332 | A1 | 8/2015 |
| WO | 2016/003294 | A1 | 1/2016 |
| WO | 2016044173 | A1 | 3/2016 |
| WO | 2016/140334 | A1 | 2/2018 |
| WO | 2018156687 | A1 | 8/2018 |
| WO | 2019/147609 | A2 | 8/2019 |
| WO | 2020/150657 | A1 | 7/2020 |
| WO | 2022/212851 | A1 | 10/2022 |

OTHER PUBLICATIONS

Extended European Search Report of European Patent Application No. 20741953.2 dated Sep. 9, 2022.

International Search Report of PCT/US2020/014173 dated Apr. 23, 2020.

Written Opinion of PCT/US2020/014173 dated Apr. 23, 2020.

First Office Action, dated Jun. 6, 2017, for related Chinese Patent Application No. 202080021797.7, with English translation attached.

Second Office Action, dated Apr. 26, 2024, for related Chinese Patent Application No. 202080021797.7, with English translation attached.

Third Office Action, dated Sep. 30, 2024, for related Chinese Patent Application No. 202080021797.7, with English translation attached.

International Search Report and Written Opinion, dated Apr. 23, 2019, for International Application Serial No. PCT/US2019/014663 filed Jan. 23, 2019.

First Examiner's Report, mailed Feb. 7, 2025, for Canadian Patent Application No. 3089342.

Supplementary European Search Report mailed Sep. 16, 2021 for European Patent Application No. 19743528.2.

International Search Report and Written Opinion, dated Sep. 12, 2022, for International Application Serial No. PCT/US2022/023064, filed Apr. 1, 2022.

Office Action, mailed Jan. 31, 2025, for related European Application No. 20741953.2.

First Examiner's Report, mailed Nov. 21, 2024, for related Australian Patent Application No. 2020207944.

First Examiner's Report, mailed dated Feb. 4, 2025, for related Canadian Patent Application No. 3126939.

Notification of Decision of Rejection, dated Sep. 3, 2024 for related Japanese Patent Application No. 2024-541251, with English translation attached.

Notification of Decision of Rejection, dated Feb. 21, 2023, for Japanese Patent Application No. 2020-561580, with English translation attached.

Notification of Decision of Rejection, dated Sep. 19, 2023, for Japanese Patent Application No. 2020-561580, with English translation attached.

Office Action, mailed May 23, 2024, for European Application No. 19743528.2.

First Office Action, dated Feb. 27, 2024, for related Chinese Patent Application No. 201980020255.5, with English translation attached.

Second Office Action, dated May 21, 2024, for related Chinese Patent Application No. 201980020255.5, with English translation attached.

Third Office Action, dated Jan. 11, 2025, for related Chinese Patent Application No. 201980020255.5, with English translation attached.

* cited by examiner

METHOD AND DEVICE FOR TREATING EYE DISEASE

PRIORITY CLAIM

This application is a national phase entry of PCT/US2020/014173, filed on Jan. 17, 2020, which claims the benefit of U.S. provisional patent application No. 62/794,139, filed on Jan. 18, 2019, the entire disclosure of which is are incorporated herein by reference.

BACKGROUND

Millions of individuals suffer from eye disease, specifically glaucoma. Most glaucoma patients have abnormally high intraocular pressure (IOP) due to the patient's inability to drain excessive aqueous humor from the anterior chamber of the eye through the trabecular meshwork. If not reduced with adequate treatment, the high IOP will continuously damage the optic nerve as the disease progresses, leading to loss of vision or even total blindness. Current medications, surgeries, and implants have proven inadequate in lowering pressure within the eye or sustaining normal eye pressure over many years. Therefore, the need exists for new ways to alleviate IOP, thereby treating glaucoma.

SUMMARY

Described herein are treatment devices, or simply devices, useful for treating ocular conditions. In one embodiment, an ocular condition is elevated intraocular pressure, and the devices herein lower the intraocular pressure. The devices generally include: a plate structure or core component comprising a first major surface coated with a first material and a second major surface coated with a second material. In some embodiments, the plate or core component is simply coated, thereby not defining a first and second coating.

The plate structure or plate can have a thickness ranging from about 1 nm to about 1,000 nm, or from about 50 nm to about 800 nm.

The plate structure can include channels that assist with movement of ocular fluids which, in turn, reduces intraocular pressure.

Other embodiments include methods of reducing intraocular pressure. In one embodiment, a method includes securing a device as described herein to an eye thereby moving ocular fluids and reducing intraocular pressure.

In some embodiments, devices are described for lowering or reducing intraocular pressure. The devices can include: a plate structure comprising a first surface opposite a second surface, wherein the first surface includes a series of fluid channels, a first coating on the first surface, and a second coating on the second surface.

In some embodiments, the plate structure is formed of a ceramic material. The ceramic material can be selected from alumina, silicon nitride, silica, hafnium oxide, titanium nitride, and titanium.

In some embodiments, the first coating is a polymeric material. The polymeric material can be a parylene polymer. The parylene polymer can be parylene C, parylene D, parylene N, a derivative thereof or a combination thereof.

In other embodiments, the polymeric material includes rubber, synthetic rubber, silicone polymers, parylene, thermoplstics, thermosets, polyolefins, polyisobutylene, acrylic polymers, ethylene-co-vinylacetate, polybutylmethacrylate, vinyl halide polymers, polyvinyl ethers, polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides, alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene, poly(ether-ether-ketone), poly lactides such as PLA, PLGA, PLLA, derivatives thereof, or combinations thereof.

In some embodiments, the second coating includes aluminum oxide and/or a parylene polymer.

In some embodiments, the second coating includes aluminum oxide in combination with rubber, synthetic rubber, silicone polymers, parylene, thermoplstics, thermosets, polyolefins, polyisobutylene, acrylic polymers, ethylene-co-vinylacetate, polybutylmethacrylate, vinyl halide polymers, polyvinyl ethers, polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides, alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene, poly(ether-ether-ketone), poly lactides such as PLA, PLGA, PLLA, derivatives thereof, or combinations thereof.

The series of fluid channels can include a plurality of open-ended channels interconnected to form an intersecting network of fluid pathways. In some embodiments, the channels are microchannel s.

In some embodiments the device further includes a drug. In some embodiments, that drug(s) can be within a microchannel. In some embodiments, that drug(s) can be held in a microchannel by a coating.

Methods of treatment are also described. In one embodiment, methods are described including injecting a device into an eye with high intraocular pressure, the device including a plate structure comprising a first surface opposite a second surface, wherein the first surface includes a series of fluid channels, a first coating on the first surface, and a second coating on the second surface, and treating the high or elevated intraocular pressure.

The methods can further include securing the device to the eye. The securing can be to the sclera or any other portion of the eye.

In some embodiments, at least a portion of the first surface faces the conjunctiva of the eye and at least a portion of the second surface faces the sclera of the eye.

In other embodiments, the device forms a fluid pathway that provides fluid communication between the anterior chamber of the eye and the device position.

Further, the fluid pathway comprises the series of fluid channels.

In some embodiments, treating the high intraocular pressure is a treatment for glaucoma.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
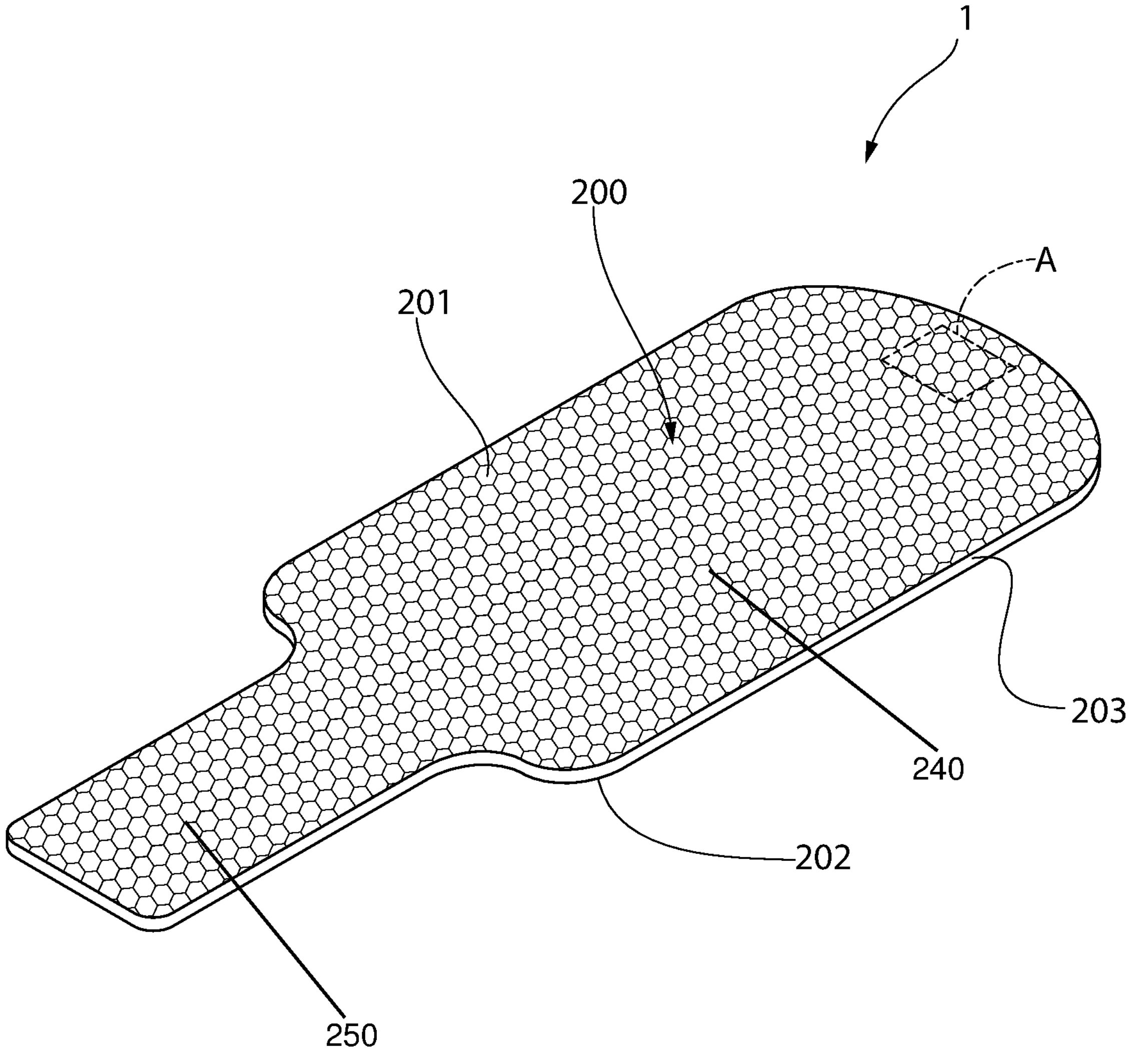
FIG. 1 is a perspective view of a device according to one embodiment.

The following description of the embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the structure be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Unless otherwise specified, all percentages and amounts expressed herein and elsewhere in the specification should be understood to refer to percentages by weight. The amounts given are based on the weight of the material. According to the present application, the term "about" means +/−5% of the reference value. According to the present application, the term "substantially free" means less than about 0.1 wt. % based on the total of the referenced value.

A "subject" herein may be a human or a non-human animal, for example, but not by limitation, rodents such as mice, rats, hamsters, and guinea pigs; rabbits; dogs; cats; sheep; pigs; goats; cattle; horses; and non-human primates such as apes and monkeys, etc.

Figure 2:
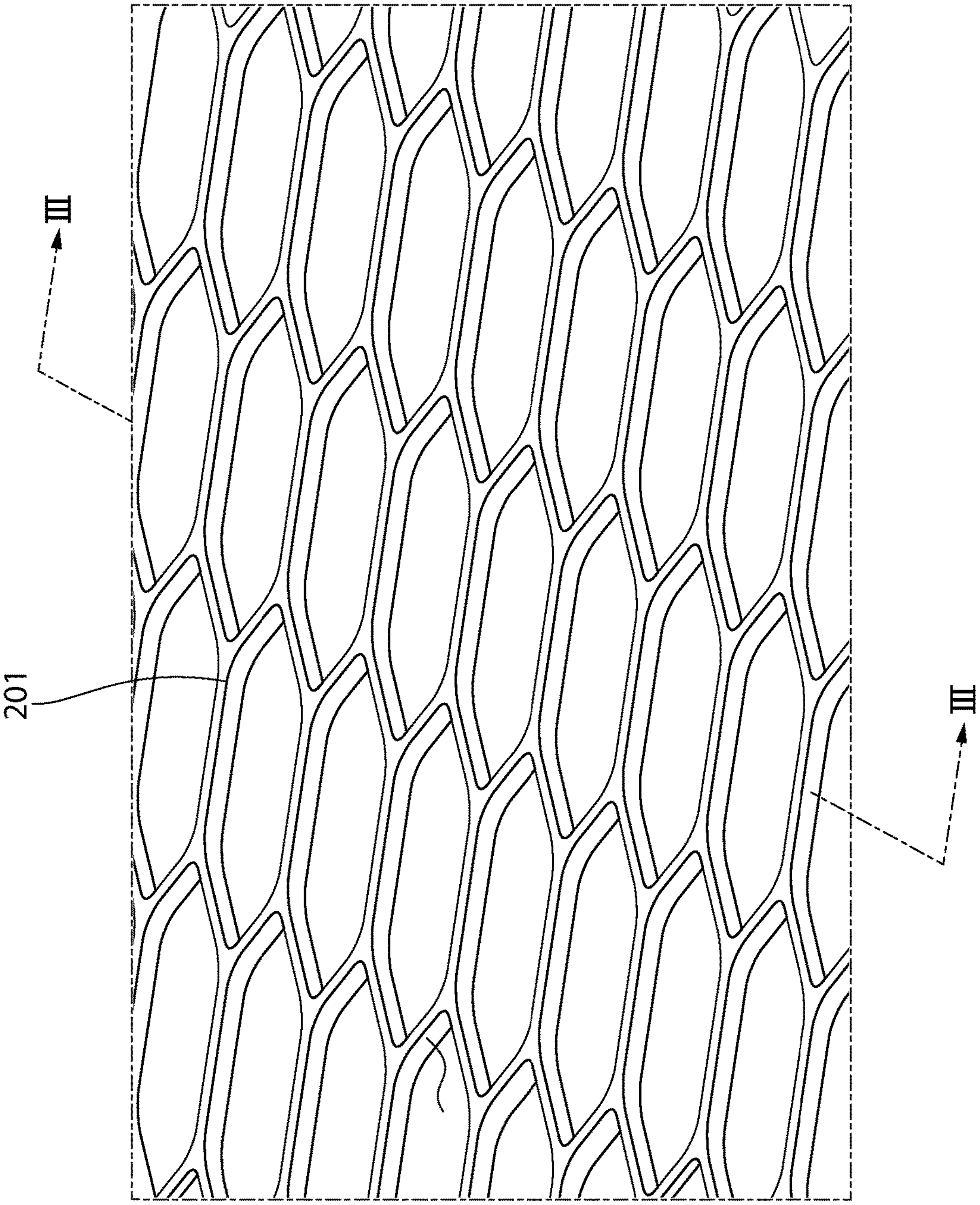
FIG. 2 is a close-up view of the device according to section A identified in FIG. 1.
Figure 3:
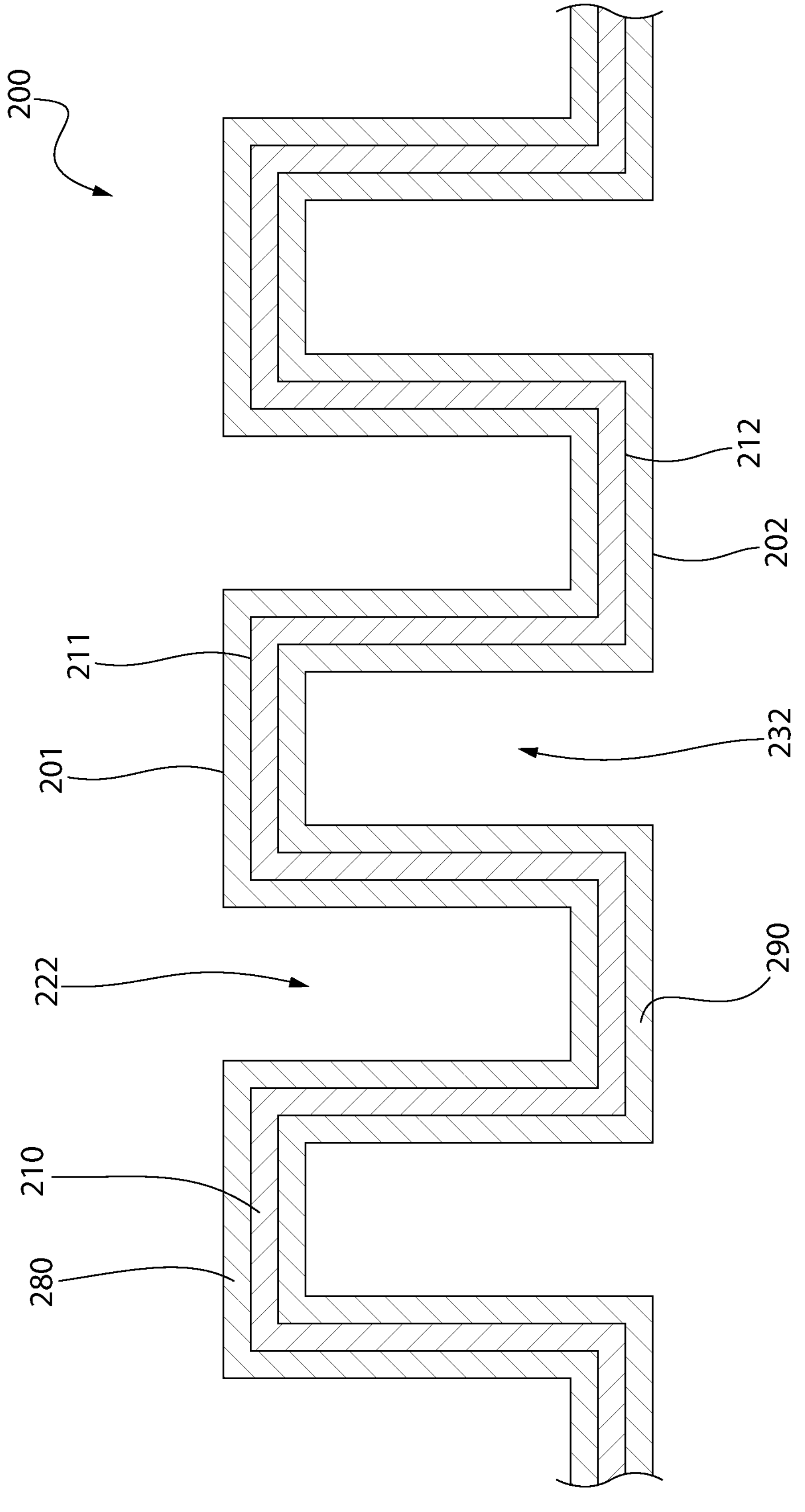
FIG. 3 is a cross-sectional view of the device shown along line in FIG. 2.
Figure 4:
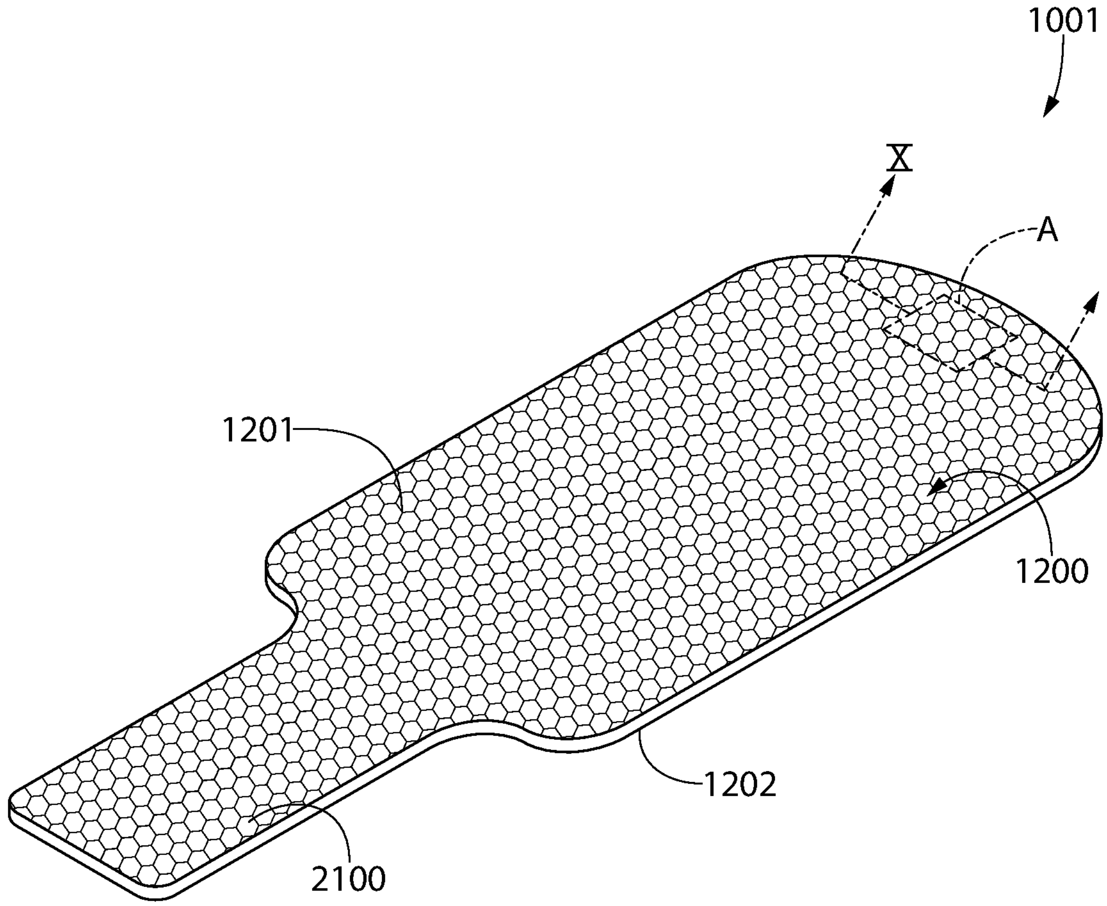
FIG. 4 is a perspective view of a device according to another embodiment.

Referring to FIGS. 1-3, treatment device 1, or simply device, may comprise plate structure 200, or simply plate, having first major exposed surface 201 opposite second major exposed surface 202 as well as side surface 203 extending there-between. Plate structure 200 can comprise extension portion 250 and main body portion 240.

Plate structure 200 can be formed of any material with appropriate characteristics for implantation and treatment. In some embodiments, plate structure 200 can be formed of a metal, polymer, ceramic, other composite material, or a combination thereof. Metals can include, but are not limited to aluminum, titanium, zinc, platinum, tantalum, copper, nickel, rhodium, gold, silver, palladium, chromium, iron, indium, ruthenium, osmium, tin, iridium, or combinations, and alloys thereof. In some embodiments, alloys can include steel and nickel titanium such as Nitinol.

Polymers or polymer materials used to form plate structure 200 can include any of the polymers described herein.

Composites such as silicon composites can also be used. In one embodiment, a composite can include silicon nitride ($Si_3N_4$). The silicon nitride can have any known crystalline structure such as, but not limited to, trigonal $\alpha$-$Si_3N_4$, hexagonal $\beta$-$Si_3N_4$, or cubic $\gamma$-$Si_3N_4$.

The plate structure, or plate, can have a thickness ranging from about 1 nm to about 1,000 nm, from about 1 nm to about 500 nm, from about 1 nm to about 400 nm, from about 100 nm to about 1,000 nm, from about 200 nm to about 1,000 nm, from about 300 nm to about 1,000 nm, from about 400 nm to about 1,000 nm, from about 1 nm to about 900 nm, from about 1 nm to about 800 nm, from about 1 nm to about 700 nm, from about 1 nm to about 600 nm, from about 300 nm to about 500 nm, from about 300 nm to about 600 nm, from about 400 nm to about 600 nm, from about 200 nm to about 600 nm, from about 200 nm to about 500 nm, or from about 50 nm to about 800 nm.

Plate structure 200 may comprise multi-directional plate 210 comprising first major surface 211 opposite second major surface 212. Multi-directional plate 210 may form a plurality of topographical features (for example, a repeating honeycomb pattern) on each of first major surface 211 and second major surface 212. Each of the first and second topographies may independently comprise plurality of channels 232 and/or plurality of open-cells 222.

Plurality of channels 232 may be interconnected and can form a network of channels. The channels may be open, allowing fluid to readily enter each channel of plurality of channels 232 and flow through it. The network may comprise intersecting channels in any suitable configuration to best help promote the flow of fluid across plate structure 200 via the plurality of channels 232. In one embodiment, the channels may be configured to form hexagonal patterns. Once treatment device 1, illustrated in FIG. 1, is implanted, fluid (e.g., aqueous humor) may be driven by a pressure gradient to flow through the channels and across the surface of plate structure 200.

In some embodiments, the channels can include a ribbing pattern. The ribbing pattern and/or the geometry of the channels in the plate can be varied based on different severities of glaucoma. In one embodiment, larger or smaller channels can be used to decrease intraocular pressure by different amounts. Changing intraocular pressure by a lower amount can decrease risk of hypotony (a condition that can exist if intraocular pressure is reduced too much) and increase efficacy at lowering pressure. In some embodiments, a device as described herein with smaller channels can decrease flow and decrease risk of hypotony. Likewise, larger channels can increase flow and increase efficacy of the device to lower intraocular pressure.

Plate structure 200 may further comprise first coating 280 applied to first major surface 211 of multi-directional plate 210. First coating 280 may conform to the first topography of first major surface 211 of the multi-directional plate 210. In other embodiments, first coating 280 may form a topography that does not conform to the first topography of first major surface 211 of multi-directional plate 210.

First coating 280 may have a thickness ranging from about 0.1 μm to about 10 μm or about 0.1 μm to about 1 μm—including all thickness and sub-ranges there-between. In one embodiment, the thickness is between about 0.4 μm (400 nm) and 0.6 μm (600 nm). In one embodiment, the thickness is about 0.4 μm (400 nm). In other embodiments, the thickness is between about 1 μm and about 5 μm, between about 1 μm and about 3 μm, between about 2 μm and about 5 μm, or between about 2 μm and about 4 μm. In one embodiment, the thickness is about 2 μm.

Plate structure 200 may further comprise second coating 290 applied to second major surface 212 of multi-directional plate 210. Second coating 290 may conform to the plurality of surface features on second major surface 212 of multi-directional plate 210. In other embodiments, second coating 290 may form a topography that does not conform to the second topography of second major surface 212 of multi-directional plate 210.

Second coating 290 may have a thickness ranging from about 0.1 μm to about 10 μm or about 0.1 μm to about 1 μm—including all thickness and sub-ranges there-between. In one embodiment, the thickness is between about 0.4 μm (400 nm) and 0.6 μm (600 nm). In one embodiment, the thickness is about 0.4 μm (400 nm). In other embodiments, the thickness is between about 1 μm and about 5 μm, between about 1 μm and about 3 μm, between about 2 μm and about 5 μm, or between about 2 μm and about 4 μm. In one embodiment, the thickness is about 2 μm.

In some embodiments, plate structure 200 may comprise only first coating 280—i.e., no second coating. In other embodiments, plate structure 200 may comprise only second coating 290—i.e., no first coating. In other embodiments, plate structure 200 may comprise first coating 280 and second coating 290, whereby the first and second coatings overlap to fully encapsulate multi-directional plate 210. In such embodiments, side surface 203 of plate structure 200 may comprise at least one of first coating 280 and second coating 290.

In some embodiments, first and second coating, and any edge coating, can be thicker than the plate itself. In some embodiments, the coating thickness can be one, two or three orders of magnitude thicker than the plate structure. However, in other embodiments, the plate can be thicker than each coating or the additive thickness of the two coatings.

Coatings described herein can be applied by any suitable deposition method, such as but not limited to, chemical vapor deposition, atomic layer deposition, spray coating, dip coating or brushing.

First coating 280 may be applied to first major surface 211 by any suitable deposition method. In a non-limiting example, first coating 280 may be applied to first major surface 211 by chemical vapor deposition. In another non-limiting example, first coating 280 may be applied to first major surface 211 by atomic layer deposition. In another non-limiting example, first coating 280 may be applied to first major surface 211 by spray coating. In another non-limiting example, first coating 280 may be applied to first major surface 211 by dip coating. In another non-limiting example, first coating 280 may be applied to first major surface 211 by brushing.

Second coating 290 may be applied to second major surface 212 by any suitable deposition method. In a non-limiting example, second coating 290 may be applied to second major surface 212 by chemical vapor deposition. In another non-limiting example, second coating 290 may be applied to second major surface 212 by atomic layer deposition. In another non-limiting example, second coating 290 may be applied to second major surface 212 by spray coating. In another non-limiting example, second coating 290 may be applied to second major surface 212 by dip coating. In another non-limiting example, second coating 290 may be applied to second major surface 212 by brushing.

First coating 280 may be the same as second coating 290. First coating 280 and second coating 290 may be different.

First coating 280 may be hydrophilic. First coating 280 may be hydrophobic. First coating 280 may be lipophilic. First coating 280 may be lipophobic. Second coating 290 may be hydrophilic. Second coating 290 may be hydrophobic. Second coating 290 may be lipophilic. Second coating 290 may be lipophobic. Each of first and second coatings 280, 290 may independently be continuous. Each of first and second coatings 280, 290 may independently be discontinuous. In some embodiments, first and second coatings 280, 290 may both be hydrophobic. In some embodiments, first and second coatings 280, 290 may both be hydrophilic. In some embodiments, first and second coatings 280, 290 may both be lipophilic.

First coating 280 may be organic. First coating 280 may be inorganic. Second coating 290 may be organic. Second coating 290 may be inorganic.

In some embodiments, first coating 280 is hydrophilic and second coating 290 is hydrophobic. In some embodiments, first coating 280 is hydrophilic and second coating 290 is hydrophilic. Having at least one of first and/or second coating 280, 290 be hydrophobic may help prevent treatment device 1 from inadvertently sticking to tissue during implantation.

In some embodiments, a purpose of a first and/or second coating is to increase the toughness of the device. Also, a first and/or second coating can increase biocompatibility of the device and/or decrease scarring by decreasing tissue and/or fibroblast adhesion. In some embodiments, the coatings described herein are hydrophobic and decrease tissue adhesion. In some embodiments, tissue adhesion can be reduced by greater than about 50%, greater than about 60%, greater than about 70%, greater than about 80%, greater than about 90%, greater than about 95%, greater than about 96%, greater than about 97%, greater than about 98%, or greater than about 99% when compared to an uncoated plate.

In a non-limiting embodiment, the first and/or second coating may comprise a parylene polymer, such as a parylene polymer (poly(para-xylylene)) or a derivative thereof. In other embodiments, the first and/or second coating can include aluminum oxide. In one embodiment, the parylene polymer is a chlorine modified poly(para-xylylene), fluorine modified poly(para-xylylene). In one embodiment, the parylene polymer can be parylene C, parylene D, parylene N, a derivative thereof or a combination thereof. In other embodiments, the first and/or second coating can include aluminum oxide.

In other embodiments, other polymer(s) can be used in addition to, in combination with, or instead of a parylene polymer and/or aluminum oxide. In some embodiments, other polymeric materials can include, but are not limited to rubber, synthetic rubber, silicone polymers, thermoplstics, thermosets, polyolefins, polyisobutylene, acrylic polymers, ethylene-co-vinylacetate, polybutylmethacrylate, vinyl halide polymers (for example, polyvinyl chloride), polyvinyl ethers (for example, polyvinyl methyl ether), polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides (for example, Nylon 66 and polycaprolactam), alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene (for example, Teflon), poly(ether-ether-ketone), poly lactides such as PLA, PLGA, PLLA, derivatives thereof, or combinations thereof.

The resulting treatment device 1 may comprise first plurality of channels 222 present on first exposed major surface 201 of plate structure 200, wherein first plurality of channels 222 are hydrophilic due to the presence of first coating 280. The resulting treatment device 1 may comprise second plurality of channels 232 present on second exposed major surface 202 of plate structure 200, wherein second plurality of channels 232 are hydrophilic due to the presence of second coating 290. As discussed, the hydrophilic channels may promote fluid flow through the channels after treatment device 1 has been implanted into a subject's eye.

Referring to FIGS. 4, 5A, 5B, and 5C, generally, treatment device 1001 is illustrated in accordance with another embodiment. Treatment device 1001 is similar to treatment device 1 except as described herein below. The description of treatment device 1 above generally applies to treatment device 1001 described below except with regard to the differences specifically noted below. A similar numbering scheme will be used for treatment device 1001 as with treatment device 1 except that a "1000" series of numbering will be used.

Treatment device 1001 comprises plate structure 1200 having first exposed major surface 1201 that is opposite second exposed major surface 1202. Plate structure 1200 may comprise multi-directional plate 1210 comprising first major surface 1211 opposite second major surface 1212. Multi-directional plate 1210 may form a plurality of topographical features (for example, a repeating honeycomb pattern) on each of first major surface 1211 and second major surface 1212. Each of the first and second topographies may independently comprise plurality of channels 1232 and/or plurality of open-cells 1222.

Figure 5A:
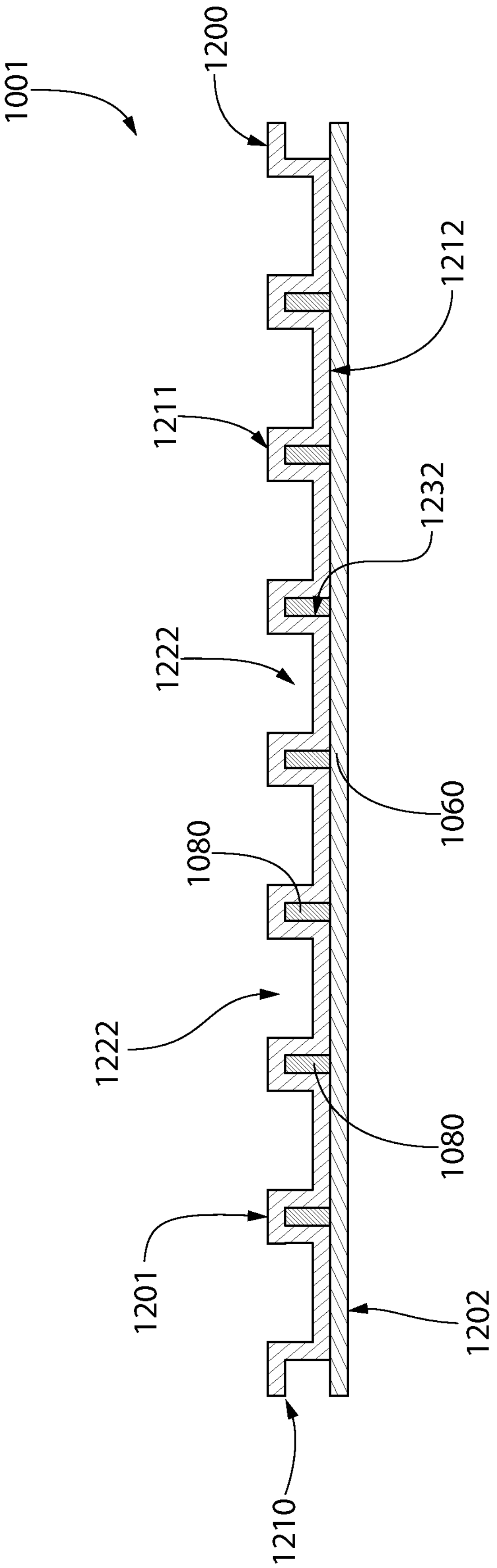
FIG. 5A is a portion of a cross-sectional view of section A of the device shown in FIG. 4 according to one embodiment.
Figure 5B:
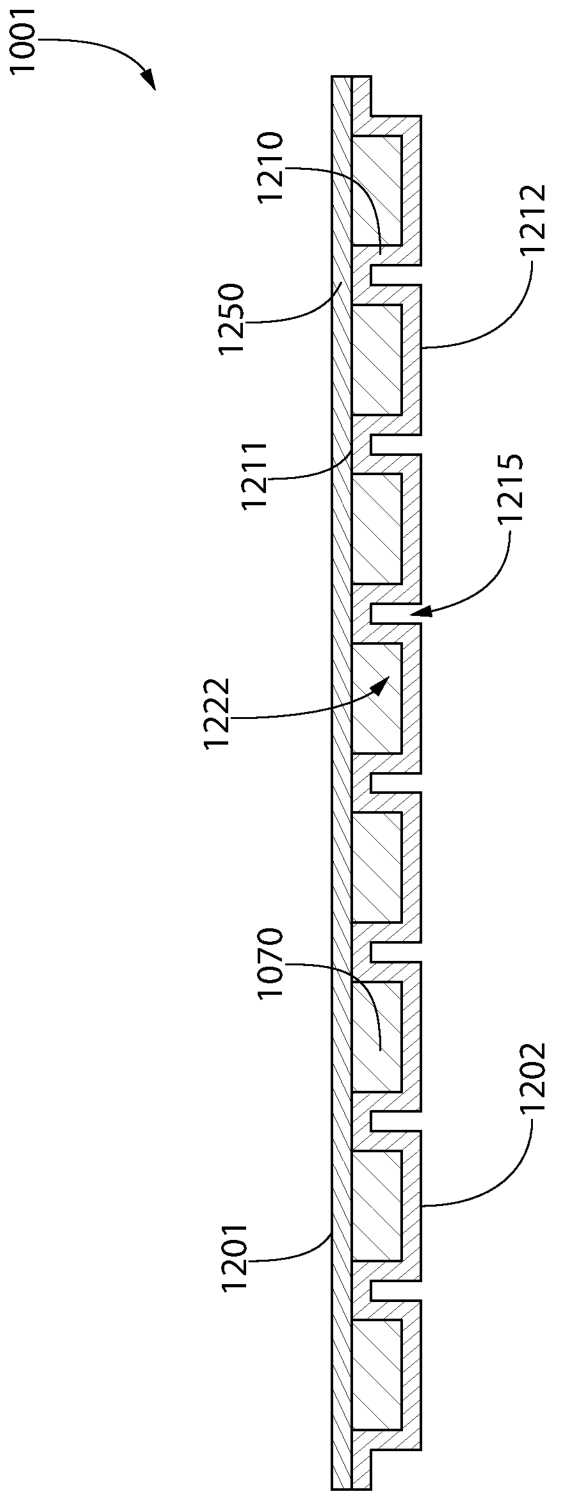
FIG. 5B is a portion of a cross-sectional view of section A of the device shown in FIG. 4 according to one embodiment.

Referring now to FIG. 5B, plate structure 1200 may comprise first delivery component 1070 present in the open voids created by the first topography formed by first exposed surface 1211 of multi-directional plate 1210. Specifically, first delivery component 1070 may be present in the open voids created by open-cells 1222 of first topography formed by first major surface 1211 of multi-directional plate 1210.

First delivery component 1070 may comprise one or more active agents such as, but not limited to therapeutic and/or pharmacological components. First delivery component 1070 may occupy some, all, or substantially all of the free volume present in open-cells 1222 formed by the first topography.

In other embodiments, active agents can include any compound or drug having a therapeutic effect in a subject. Non limiting active agents include anti-proliferatives including, but not limited to, macrolide antibiotics including FKBP-12 binding compounds, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, steroids, proteasome inhibitors, antibiotics, anti-inflammatories, anti-sense nucleotides, transforming nucleic acids, TOP lowering drugs, prostaglandins, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant microorganisms, liposomes, anti-metabolites such as mitomycin C, combinations thereof, prodrugs thereof, pharmaceutical salts thereof, derivatives thereof, and the like.

Treatment device 1001 may further comprise first coating 1050 applied to first major surface 1211 of multi-directional plate 1210. First coating 1050 may cover both first major surface 1211 of multi-directional plate 1210 as well as first delivery component 1070 that is present in open-cells 1222 formed into first major surface 1211 of multi-directional plate 1210. First coating 1050 may be in the form of a continuous film. First coating 1050 may be flat. In other embodiments, first coating 1050 may be conformal to the underlying pattern formed by multi-directional plate 1210 and first delivery component 1070.

Referring now to FIG. 5A, plate structure 1200 may comprise second delivery component 1080 present in the open voids created by the second topography formed by second exposed surface 1212 of multi-directional plate 1210. Specifically, second delivery component 1080 may be present in the open voids created by open-channels 1232 of second topography formed by second major surface 1212 of multi-directional plate 1210.

Second delivery component 1080 may be the same or different from first delivery component 1070.

Second delivery component 1080 may comprise one or more therapeutic and/or pharmacological components—including but not limited to anti-inflammatory agents, steroids, antibiotics, analgesics. Second delivery component 1080 may occupy some, all, or substantially all of the free volume present in channels 1232 formed by the first topography.

Treatment device 1001 may further comprise second coating 1060 applied to second major surface 1212 of multi-directional plate 1210. Second coating 1060 may cover both second major surface 1212 of multi-directional plate 1210 as well as second delivery component 1080 that is present in open-channels 1232 formed into second major surface 1212 of multi-directional plate 1210. Second coating 1060 may be in the form of a continuous film. Second coating 1060 may be flat. In other embodiments, second coating 1060 may be conformal to the underlying pattern formed by multi-directional plate 1210 and second delivery component 1080.

Second coating 1060 may be the same or different than first coating 1050. For each of first and second coatings 1050, 1060, the resulting film may be formed from a slow-release material that dissolves slowly after exposure to aqueous humor or other biological fluids, thereby releasing first delivery component 1070 from channels 1232 of treatment device 1001 after it has been implanted into a subject.

Figure 5C:
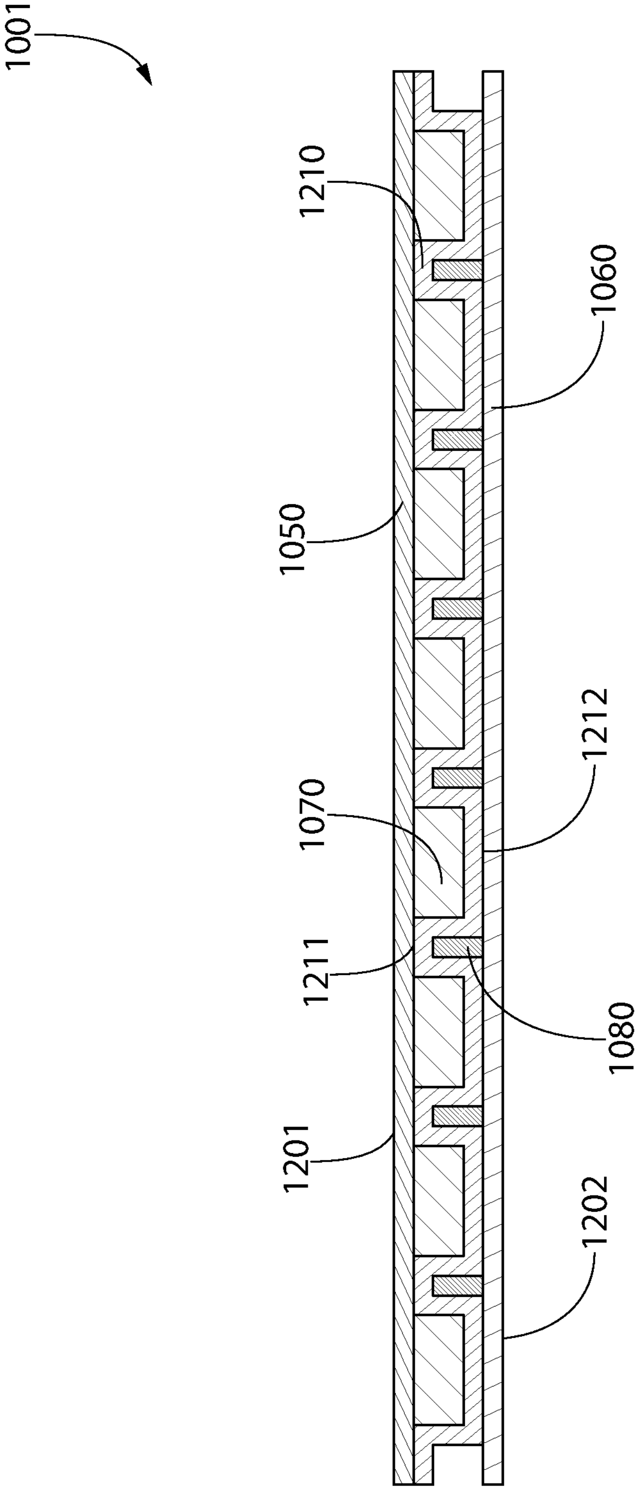
FIG. 5C is a portion of a cross-sectional view of section A of the device shown in FIG. 4 according to one embodiment.

Referring now to FIG. 5C, in other embodiments, treatment device 1001 may comprise both first and second delivery components 1070, 1080, as well as first and second coatings 1050, 1060 to encapsulate first and second delivery components 1070, 1080.

In other embodiments, plate structure 1200 may comprise at least one of first coating 1050 and/or second coating 1060 without the presence of first and/or second delivery components 1070, 1080. In such embodiments, first coating 1050 and/or second coating 1060 may form a film that covers open cells 1222 and/or open channels 1232 created by the multi-directional plate.

The presence of the films resulting from first and/or second coating 1050, 1060 may enhance the overall strength of the resulting treatment device. Specifically, layered structure(s) of the films formed by first and second coatings 1050, 1060, which are bonded to first and second major surfaces 1211, 1212 of multi-directional plate 1210—provide added mechanical integrity to the resulting treatment device.

Beyond achieving the baseline flexibility to conform to curvature of the eye, the addition of first and/or second coatings 1050, 1060 may provide a mechanism that allows the overall treatment device to match the elastic modulus of surrounding conjunctival and scleral tissues to maximize bio-integration. Findings in brain implant research confirm that the flexibility of implants in soft tissue improves compliance of the implant with microscale movements of surrounding tissue and reduces tissue displacement and trauma as well as facilitates implantation of the treatment device.

Figure 6:
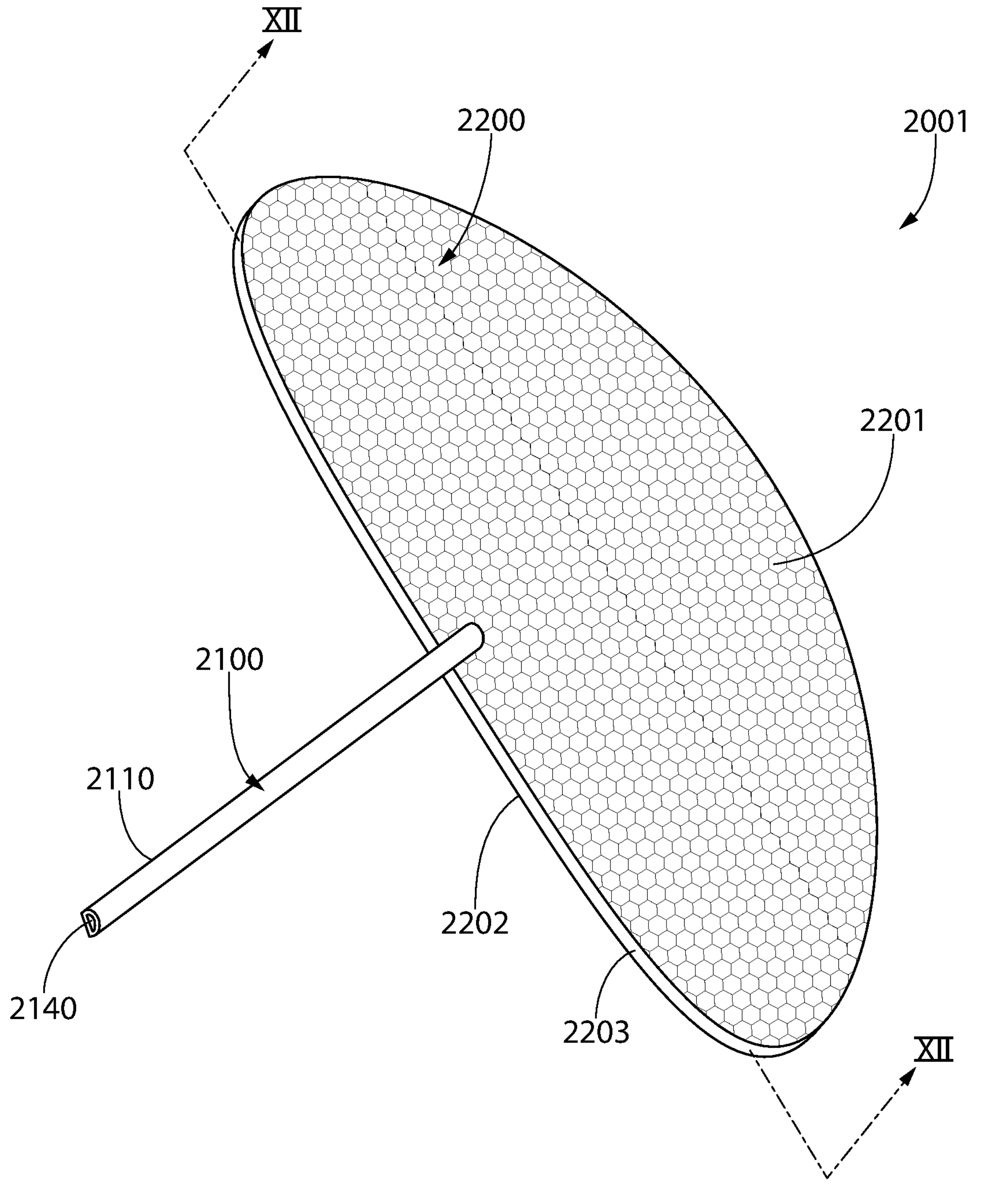
FIG. 6 is a perspective view of a device according to another embodiment of the present invention.
Figure 7:
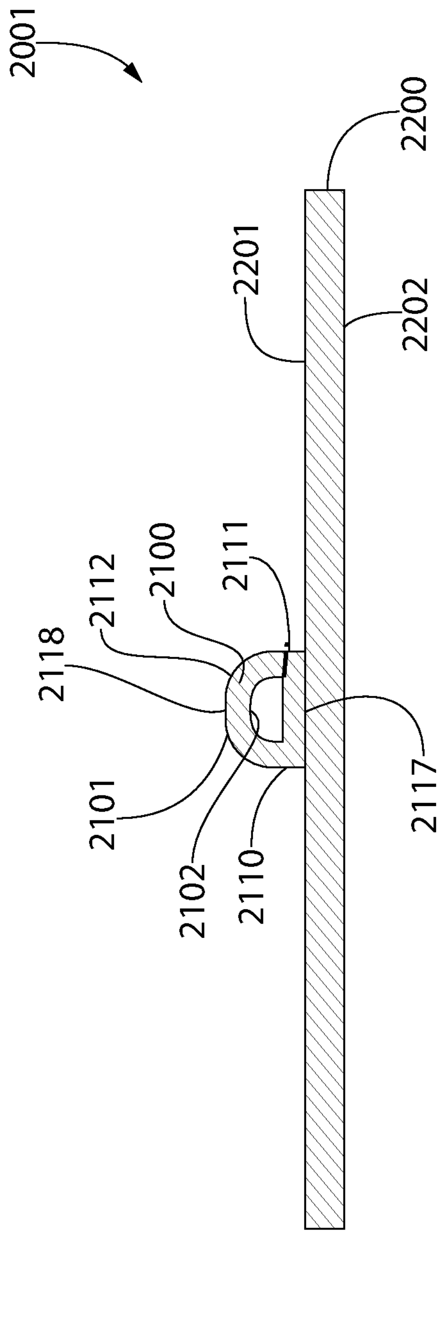
FIG. 7 is a cross-sectional view of the device shown along line XII-XII in FIG. 6 according to one embodiment.

Referring to FIGS. 6 and 7, treatment device 2001 is illustrated in accordance with another embodiment. Treatment device 2001 is similar to treatment devices 1, 1001 except as described herein below. The description of treatment devices 1, 1001, above generally apply to treatment device 2001 described below except with regard to the differences specifically noted below. A similar numbering scheme will be used for treatment device 2001 as with treatment devices 1, 1001 except that a "2000" series of numbering will be used.

Treatment device 2001 may comprise penetrating element 2100 and plate structure 2200 that are provided as separate components, whereby penetrating element 2100 is coupled to plate structure 2200. Penetrating element 2100 and plate structure 2200 may be coupled together by any suitable means, such as but not limited to adhesive, fastener, and the like. Non-limiting examples of adhesives include glue, acrylics—such as cyanoacrylates, epoxy resins, thermosets, thermoplastics, elastomers, polydimethylsiloxane (PDMS), epoxy, silicone-based, polyurethanes, or the like. Non-limiting examples of fasteners include anchors, straps, buckles, tape, or any other restraints. In some embodiments, a fastener may be used in combination with an adhesive.

Plate structure 2200 may comprise first exposed major surface 2201 that is opposite second exposed major surface 2202 as well as exposed side surface 2203 extending between first exposed major surface 2201 and second exposed major surface 2202. When viewed with the naked eye, first exposed major surface 2201 of plate structure 2200 may be substantially continuous and appear smooth. When viewed with the naked eye, second exposed major surface 2202 of plate structure 2200 may be substantially continuous and appear smooth.

Penetrating element 2100 may comprise outer surface 2101 and inner surface 2102. Penetrating element 2100 may comprise elongated body 2110. Elongated body 2110 may comprise outer surface 2112 and inner surface 2111. Penetrating element 2100 may further comprise passageway 2140 (also referred to herein as "lumen passageway") that extends through elongated body 2110. Inner surface 2111 may be continuous and form a D-shaped cross-section. The D-shaped cross-section may result in outer surface 2112 that has rounded portion 2118 and substantially flat portion 2117—whereby substantially flat portion 2117 is joined to at least one of first exposed major surface 2201 or second exposed major surface 2202 of the plate structure. Flat portion 2117 provides for better mating with smooth and/or flat major surfaces 2201, 2202 of the plate structure.

Figure 8:
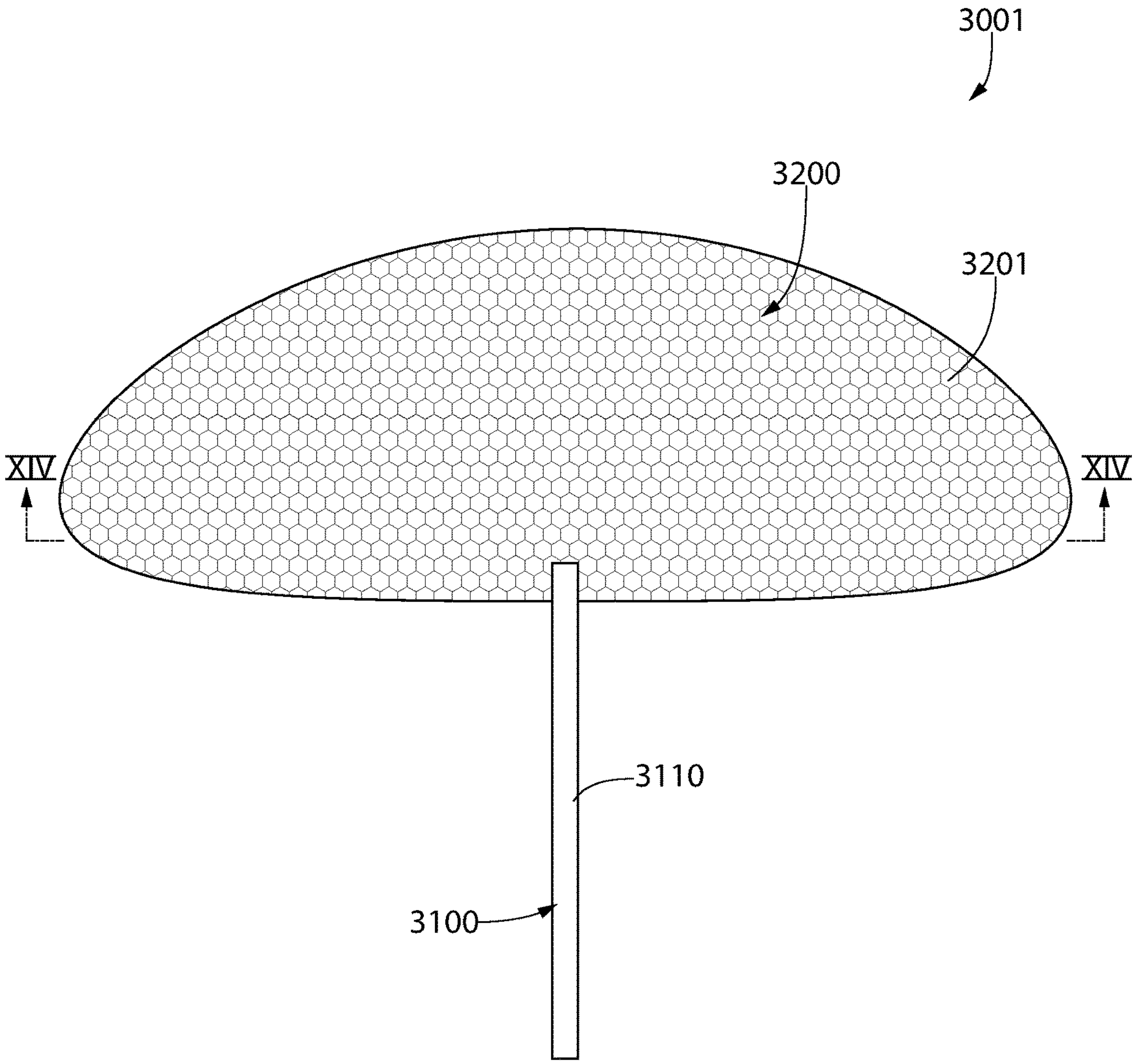
FIG. 8 is a top view of a device according to another embodiment of the present invention.
Figure 9:
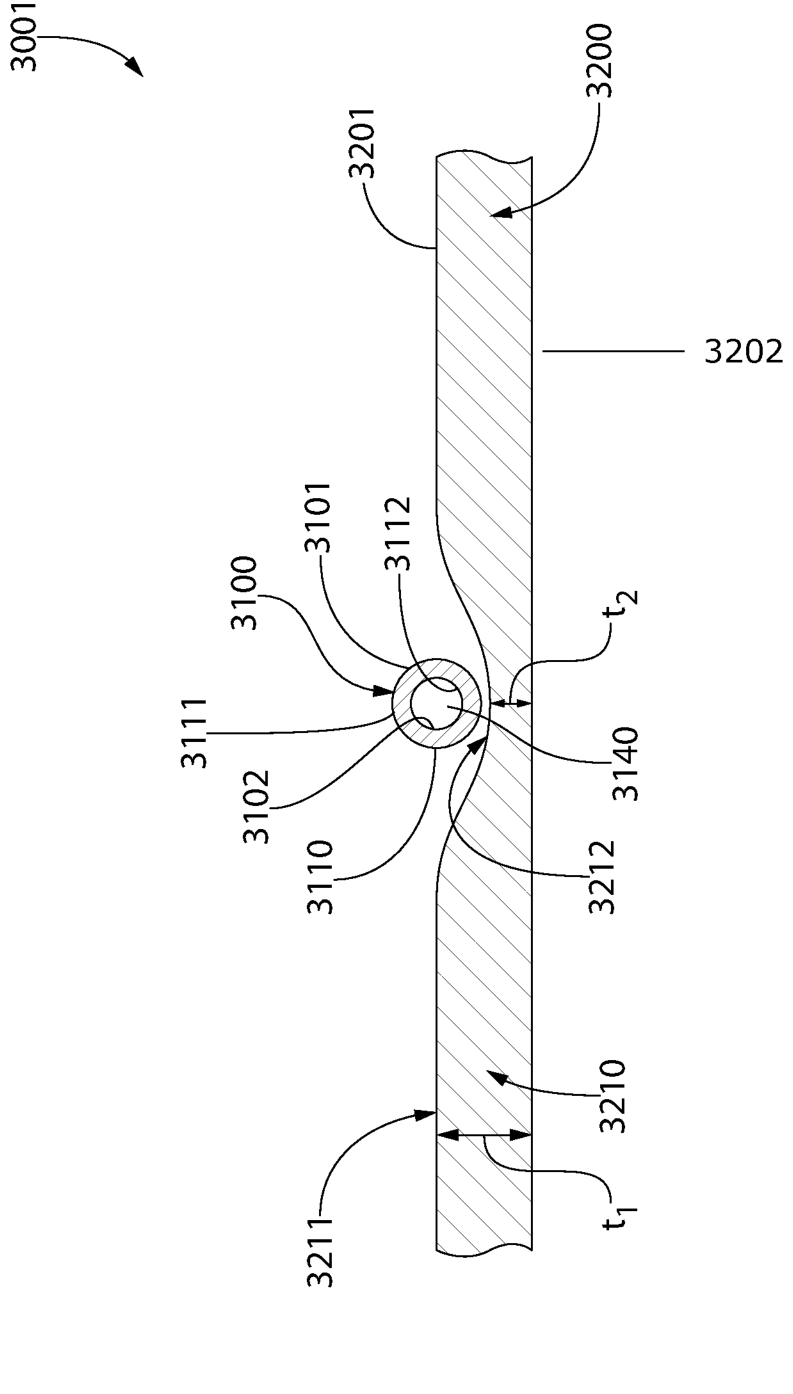
FIG. 9 is a cross-sectional view of the device shown along line XIV-XIV in FIG. 8 according to one embodiment.

Referring to FIGS. 8-9, treatment device 3001 is illustrated in accordance with another embodiment. Treatment device 3001 is similar to treatment devices 1, 1001, 2001 except as described herein below. The description of treatment devices 1, 1001, 2001 above generally applies to treatment device 3001 described below except with regard to the differences specifically noted below. A similar numbering scheme will be used for treatment device 3001 as with treatment devices 1, 1001, 2001 except that a "3000" series of numbering will be used.

Treatment device 3001 may comprise penetrating element 3100 and plate structure 3200 that are provided as separate components, whereby penetrating element 3100 is coupled to plate structure 3200. Penetrating element 3100 and plate structure 3200 may be coupled together by any suitable means, such as but not limited to adhesive, fastener, and the like. Non-limiting examples of fasteners include anchors, straps, buckles, tape, or any other restraints.

Plate structure 3200 may comprise first exposed major surface 3201 that is opposite second exposed major surface 3202. When viewed with the naked eye, first exposed major surface 3201 of plate structure 3200 may appear as or be substantially continuous and appear smooth. When viewed with the naked eye, second exposed major surface 3202 of plate structure 3200 may be substantially continuous and appear smooth.

First exposed major surface 3201 may comprise first region 3211 and second region 3212. First region 3211 may be offset from second major surface 3202 by a first thickness $t_1$. Second region 3212 may be offset from second major surface 3202 by a second thickness $t_2$. The first and second thicknesses $t_1$, $t_2$ may be different. The second thickness $t_2$ may be less than the first thickness $t_1$, such that second region 3212 forms a depression into first exposed major surface 3201 of plate structure 3200.

Penetrating element 3100 may comprise outer surface 3101 and inner surface 3102. Penetrating element 3100 may comprise elongated body 3110. Elongated body 3110 may comprise outer surface 3111 and inner surface 3112. Penetrating element 3100 may further comprise passageway 3140 (also referred to herein as "lumen passageway") that extends through elongated body 3110. Inner surface 3112 may be continuous and form a circular cross-section. The circular cross-section may result in outer surface 3111 that is also circular in shape. The depression formed by second region 3212 on first exposed major surface 3201 may accommodate for at least a portion of the circular cross-section of penetrating element 3100, thereby allowing the penetrating element to extend into plate structure 3200, thereby allowing penetrating element 3100 to have lumen passageway 3140 to allow fluid flow without having penetrating element 3100 protrude too far beyond first region 3211 of first exposed major surface 3201 of plate structure 3200.

Figure 10:
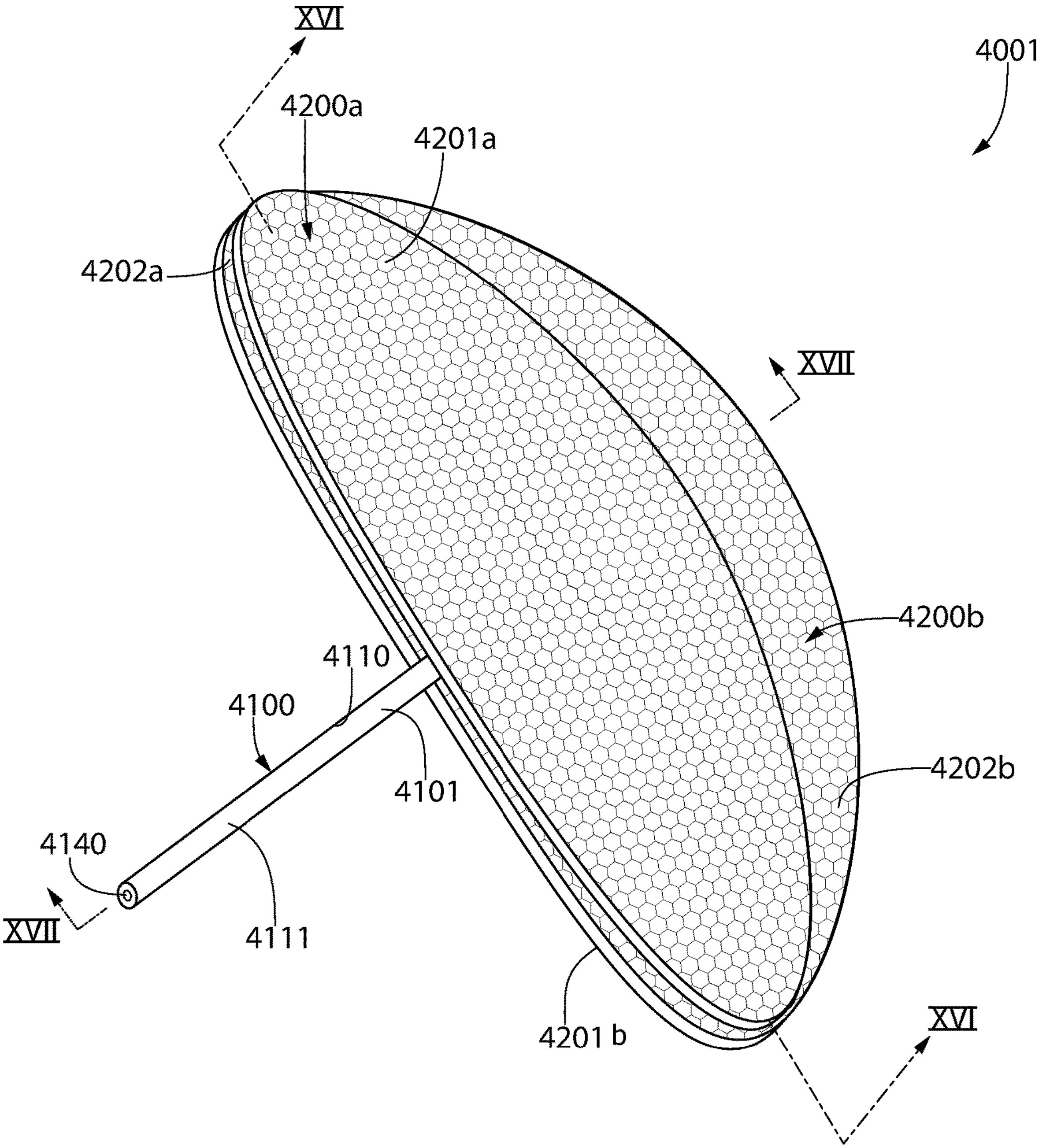
FIG. 10 is a perspective view of a device according to another embodiment.
Figure 11:
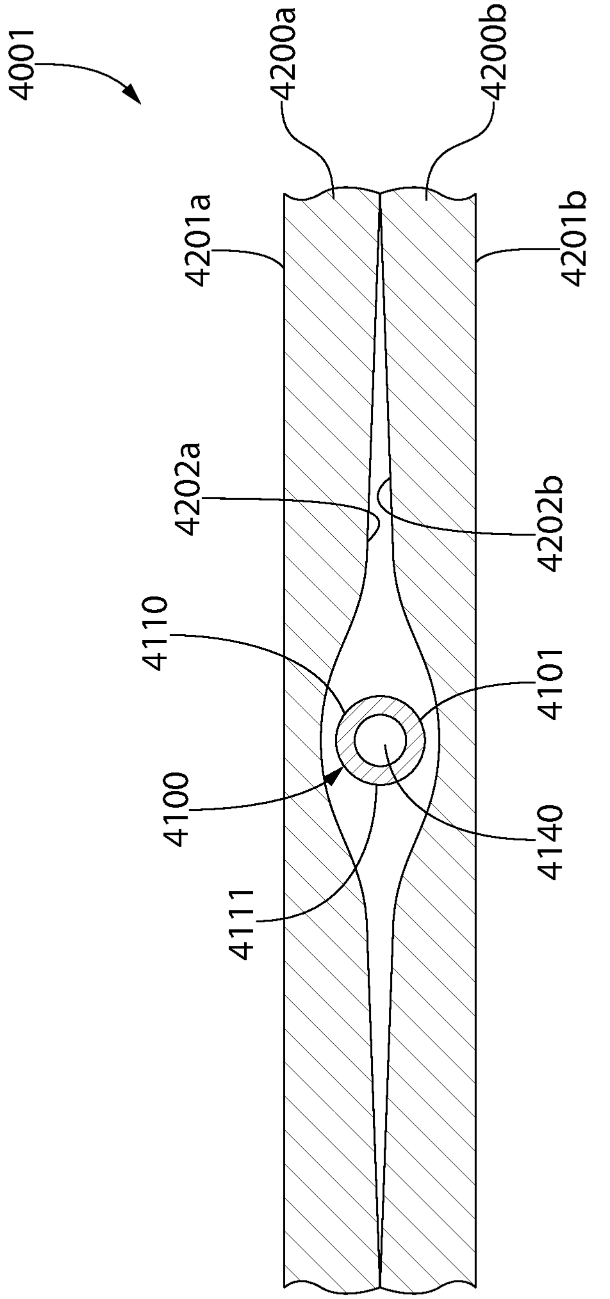
FIG. 11 is a cross-sectional view of the device shown along line XVI-XVI in FIG. 10 according to one embodiment.
Figure 12:
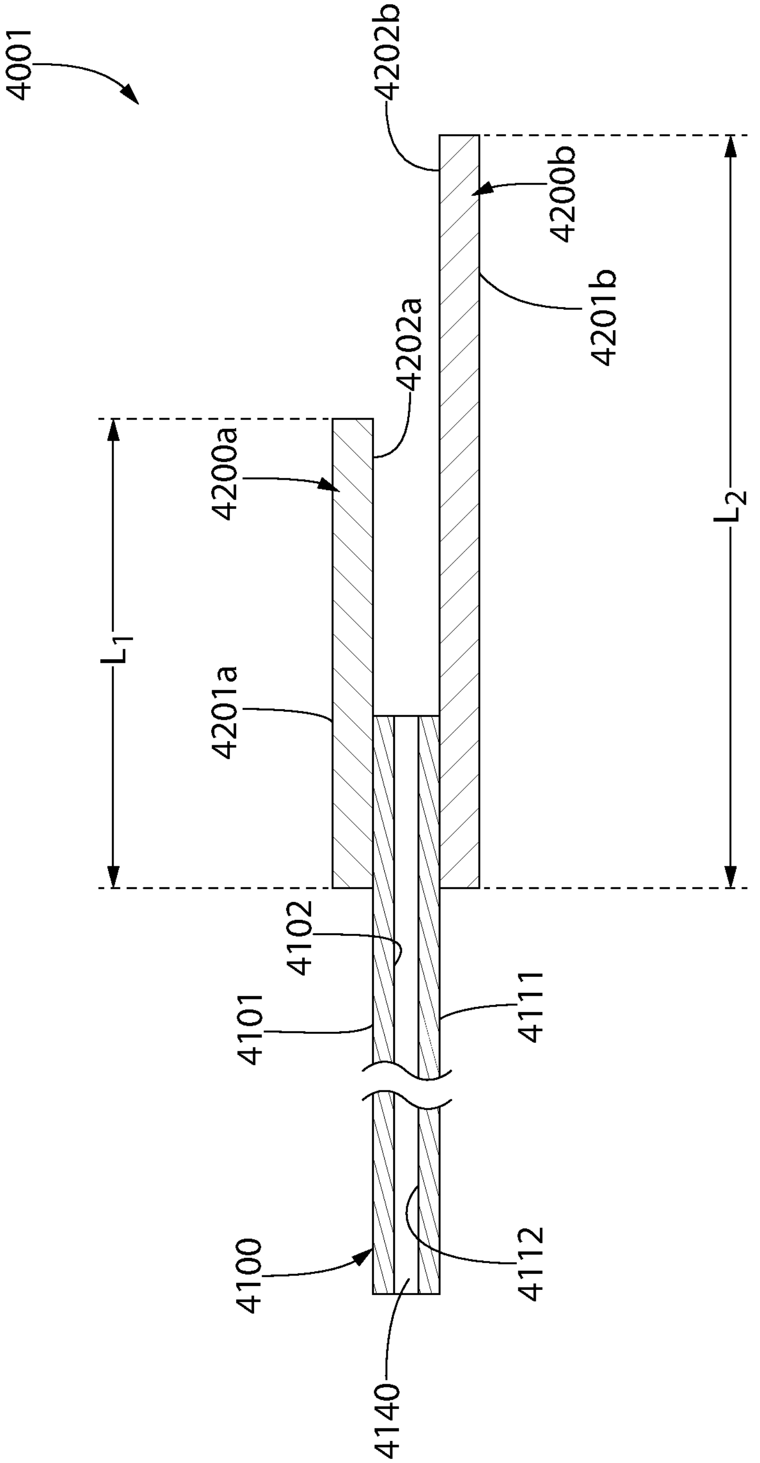
FIG. 12 is a cross-sectional view of the device shown along line XVII-XVII in FIG. 10 according to one embodiment.

Referring to FIGS. 10-12, treatment device 4001 is illustrated in accordance with another embodiment. Treatment device 4001 is similar to treatment devices 1, 1001, 2001, 3001 except as described herein below. The description of treatment devices 1, 1001, 2001, 3001 above generally applies to treatment device 4001 described below except with regard to the differences specifically noted below. A similar numbering scheme will be used for treatment device 4001 as with treatment devices 1, 1001, 2001, 3001 except that a "4000" series of numbering will be used.

Treatment device 4001 comprises first plate structure 4200*a* and second plate structure 4200*b*. First plate structure 4200*a* may comprise first major surface 4201*a* opposite second major surface 4202*a*. Second plate structure 4200*b* may comprise first major surface 4201*b* opposite second major surface 4202*b*.

First major surface 4201*a* of first plate structure 4200*a* may comprise the first topography. Second major surface 4202*a* of first plate structure 4200*a* may comprise the second topography. First major surface 4201*b* of second plate structure 4200*b* may comprise the first topography. Second major surface 4202*b* of second plate structure 4200*b* may comprise the second topography.

Second major surfaces 4202*a*, 4202*b* of first and second plate structures 4200*a*, 4200*b* may face each other. In some embodiments, at least a portion of second major surfaces 4202*a*, 4202*b* of first and second plate structures 4200*a*, 4200*b* may be in contact with each other. In some embodiments, at least a portion of second major surfaces 4202*a*, 4202*b* of first and second plate structures 4200*a*, 4200*b* may be in free-floating contact with each other. In some embodiments, at least a portion of second major surfaces 4202*a*, 4202*b* of first and second plate structures 4200*a*, 4200*b* may be offset from each other such that there is no contact between second major surfaces 4202*a*, 4202*b* of first and second plate structures 4200*a*, 4200*b*.

Treatment device 4001 may further comprise penetrating element 4100 positioned between first and second plate structures 4200*a*, 4200*b*. Penetrating element 4100 may be coupled to at least one of first and second plate structures 4200*a*, 4200*b* by any suitable means, such as but not limited to one of the aforementioned adhesives, fasteners, and the like. Penetrating element 4100 may be coupled to a portion of second major surfaces 4202*a*, 4202*b* of first and second plate structures 4200*a*, 4200*b*.

According to this embodiment, penetrating element 4100 extends between first and second plate structures 4200*a*, 4200*b* such that passageway 4140 formed by elongated body 4110 of penetrating element 4100 also extends between plate structures 4200*a*, 4200*b*. Under such configuration, fluid may enter elongated body 4110 and travel along passageway 4140 and exit between second major surfaces 4202*a*, 4202*b* of first and second plate structures 4200*a*, 4200*b*. The portion of second major surfaces 4202*a*, 4202*b* of first and second plate structures 4200*a*, 4200*b* that are in free-floating contact may separate in the presence of such fluid to allow the fluid to spread along second major surfaces 4202*a*, 4202*b* of the and second plate structures 4200*a*, 4200*b*.

First and second major surfaces 4201*a*, 4202*a* of first plate structure 4200*a* may have a first surface area, and first and second major surfaces 4201*b*, 4202*b* of second plate structure 4200*b* may have a second surface area. The first and second surface areas may be equal. In other embodiments, the first and second surface areas may be different. The second surface area may be greater than the first surface area.

First plate structure 4200*a* may have a first width and a first length $L_1$. Second plate structure 4200*b* may have a second width and a second length $L_2$. The first and second widths may be equal. In other embodiments, the first and second widths may be different. The first and second lengths $L_1$, $L_2$ may be equal (not shown). In other embodiments, as shown in FIG. 10, the first and second lengths $L_1$, $L_2$ may be different. The second length $L_2$ may be greater than the first length $L_1$—such that at least a portion of second major surface 4202*b* of second plate structure 4200*b* does not overlap with second major surface 4202*a* of first plate structure 4200*a*.

Figure 13:
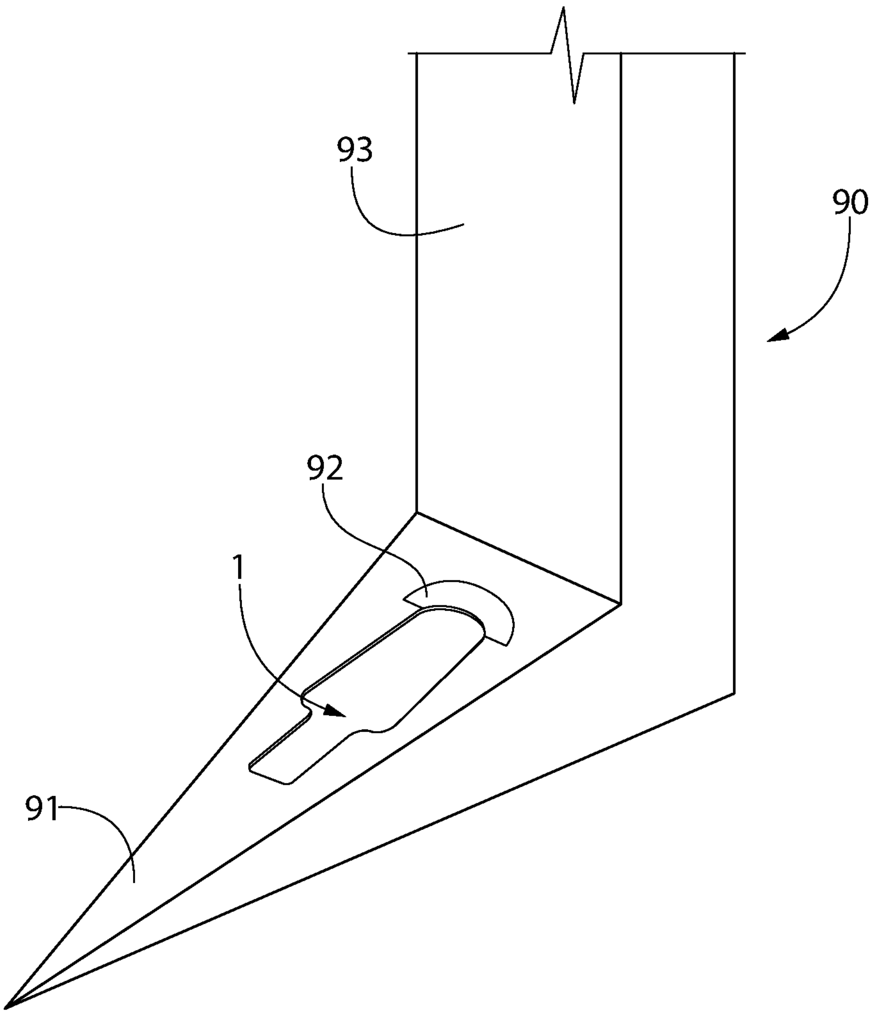
FIG. 13 is a close-up view of an implantation device for implanting a device as described herein.
Figure 14A:
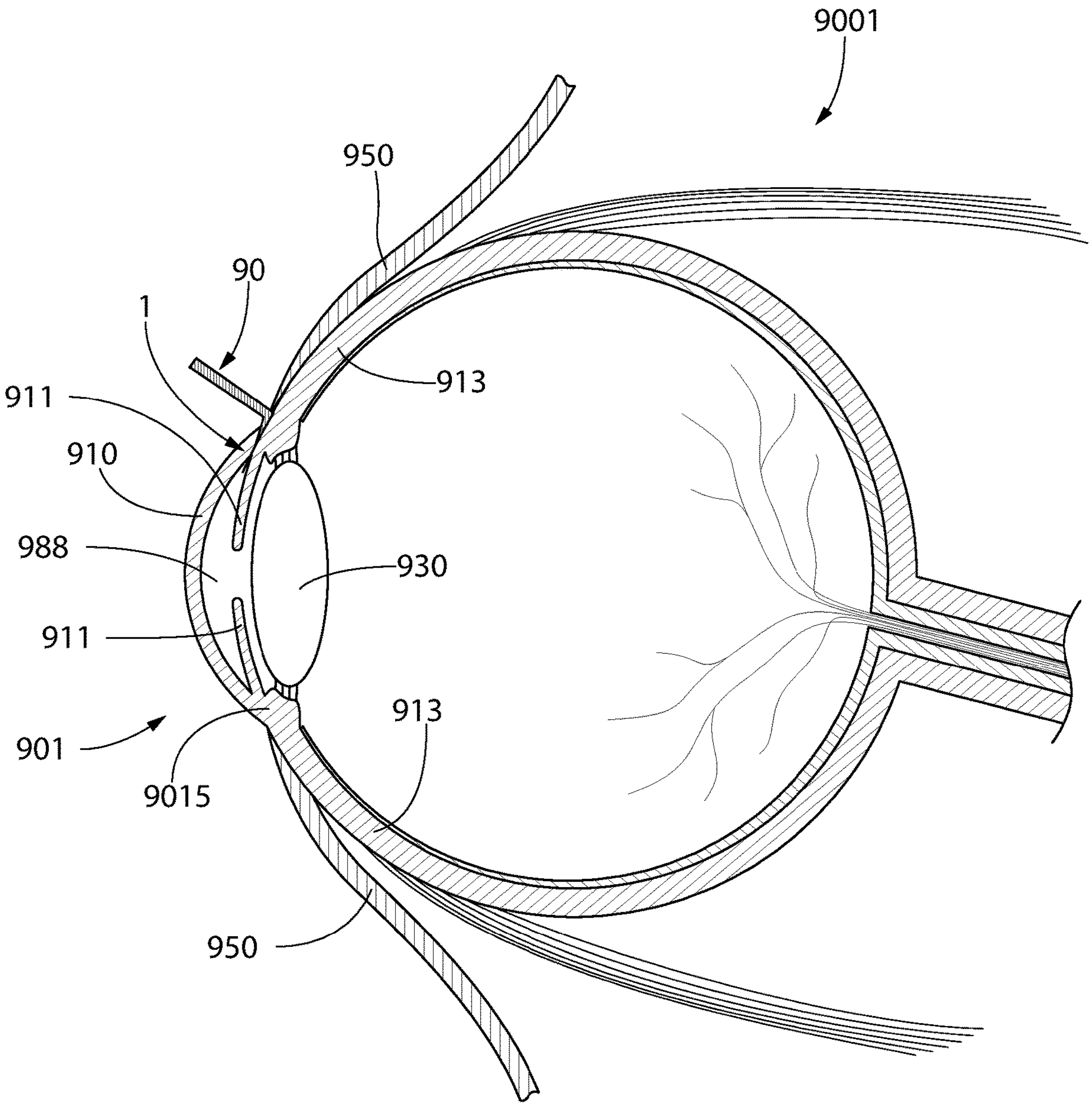
FIG. 14A is a cross-sectional view of an eye being implanted with a device using the implantation device of FIG. 13.
Figure 14B:
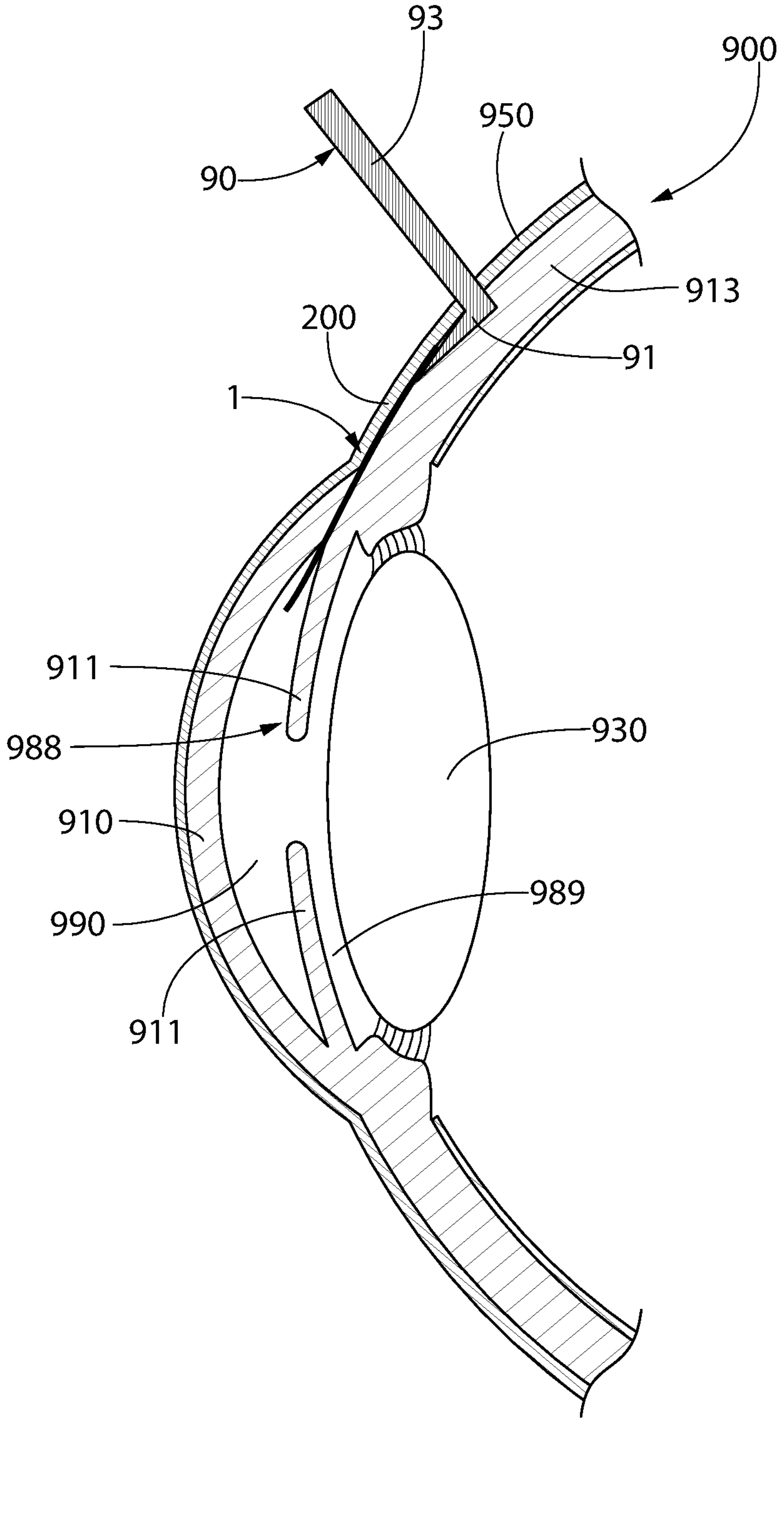
FIG. 14B is a close-up cross-sectional view of the eye being implanted with a device using the implantation device of FIG. 13.

Referring to FIGS. 13, 14A, and 14B, embodiments further comprise implantation device 90 configured to implant treatment device 1 into eye 900. The following discussion will be made in reference to treatment device 1 but also applies to treatment devices 1001, 2001, 3001, 4001 illustrated in accordance with the other embodiments of the present invention.

Implantation device 90 may comprise handle portion 93 and insertion portion 91, insertion portion 91 can comprise housing 92 for holding treatment device 1. Housing 92 may be configured to any geometry suitable to hold treatment device 1. In a non-limiting example, housing 92 may be an open-ended cavity whereby treatment device 1 is placed.

During implantation, implantation device 90 may be inserted into eye 900 such that treatment device 1 can be positioned in contact with eye 900 for the treatment of an eye disease, such as glaucoma. Specifically, insertion portion 91 may be inserted through sclera 913 and into anterior chamber 988 of eye 900 such that a distal portion of treatment device 1 is located within anterior chamber 988 of eye 900. Once treatment device 1 is in position, implantation device 90 may be removed from eye 900, whereby treatment device 1 exits housing 92 of implantation device 90 and remains in eye 900.

In position, plate structure 200 of treatment device 1 may be located between sclera 913 and conjunctiva tissue 950. Under this configuration, plate structure 200 may function as a tissue separator and/or an external reservoir for the excess fluid while the fluid is absorbed into the surrounding tissue of the subject.

Figure 15:
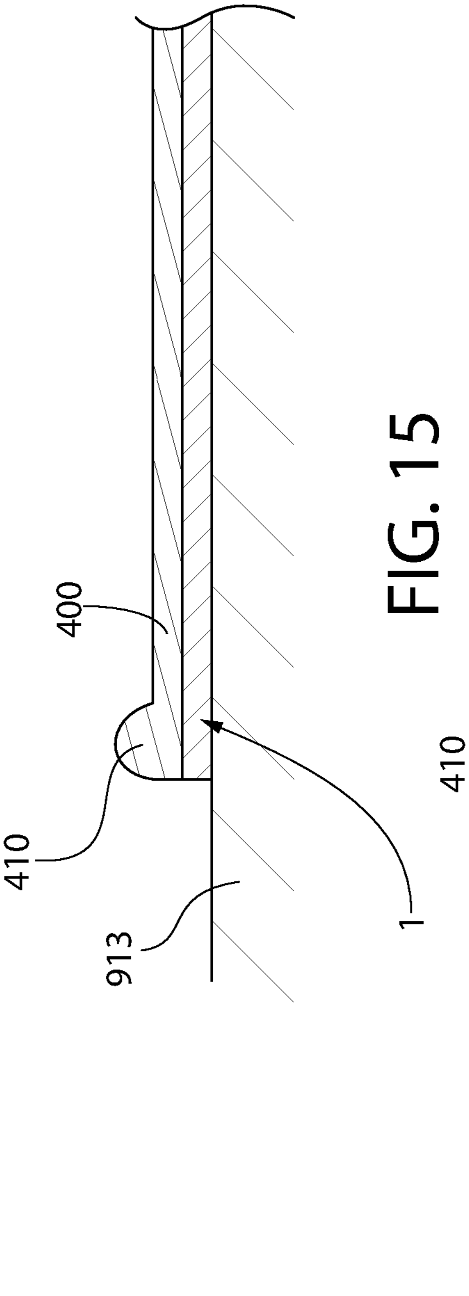
FIG. 15 is a cross-sectional view of the device of FIG. 13 during implantation.
Figure 16:
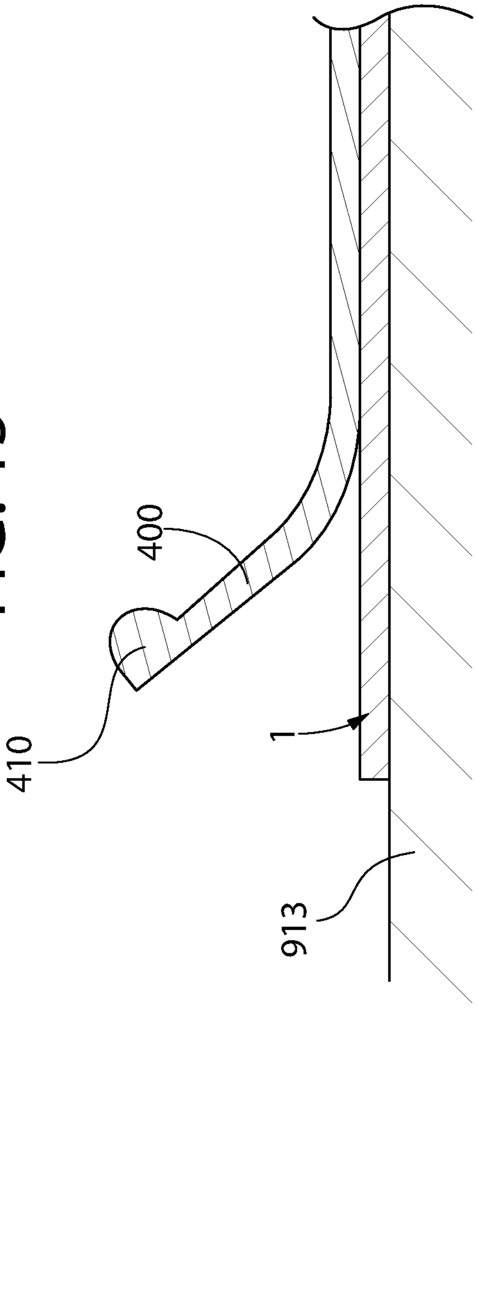
FIG. 16 is a cross-sectional view of the device of FIG. 13 during implantation.

Referring now to FIGS. 15 and 16—release decal 400 may be coupled to at least one of the major surfaces of treatment device 1. Release decal 400 may be reversibly bonded to one of major surfaces 201, 202 of plate structure 200 of treatment device 1 such that release decal 400 can be removed by peeling from the major surface of treatment device 1 but will resist shear-separation from the major surface of treatment device 1.

Release decal 400 may be formed of a material including, but not limited to, polytetrafluoroethene (PTFE), one or more metals, silicone, PDMS, glass, and/or one or more plastics.

Release decal 400 may comprise decal nub 410, which provides for a feature that allows a user to either directly or indirectly manipulate the position of treatment device 1 relative to the underlying eye tissue—specifically, sclera 913. For instance, the decal nub may be manipulated by insertion portion 91 of implantation device 1 after treatment device 1 has been released from housing 92 on implantation device 1. In other embodiments, a separate tool may be used to engage decal nub 410 to manipulate the position of treatment device 1 on sclera 913.

By having decal nub 410, the position of plate structure 200 of treatment device 1 can be precisely adjusted along sclera 913 and penetrating elements 100, 2100, 3100, 4100 of the embodiment of FIGS. 6-12 or extension portion 250 of the embodiment shown in FIG. 1 may be precisely placed within anterior chamber 988 to provide for optimal relief of excess fluid present in eye 900.

The bond strength between release decal 400 and treatment device 1 may be strong enough to resist shear, thereby allowing for lateral movement for both release decal 400 and treatment device 1. However, once precise positioning of treatment device 1 is achieved, release decal 400 may be removed from treatment device 1 by lifting release decal 400 from the treatment device in a direction that is substantially normal to the major surface of the treatment device 1—i.e., by peeling release decal 400 from treatment device 1.

Figure 17:
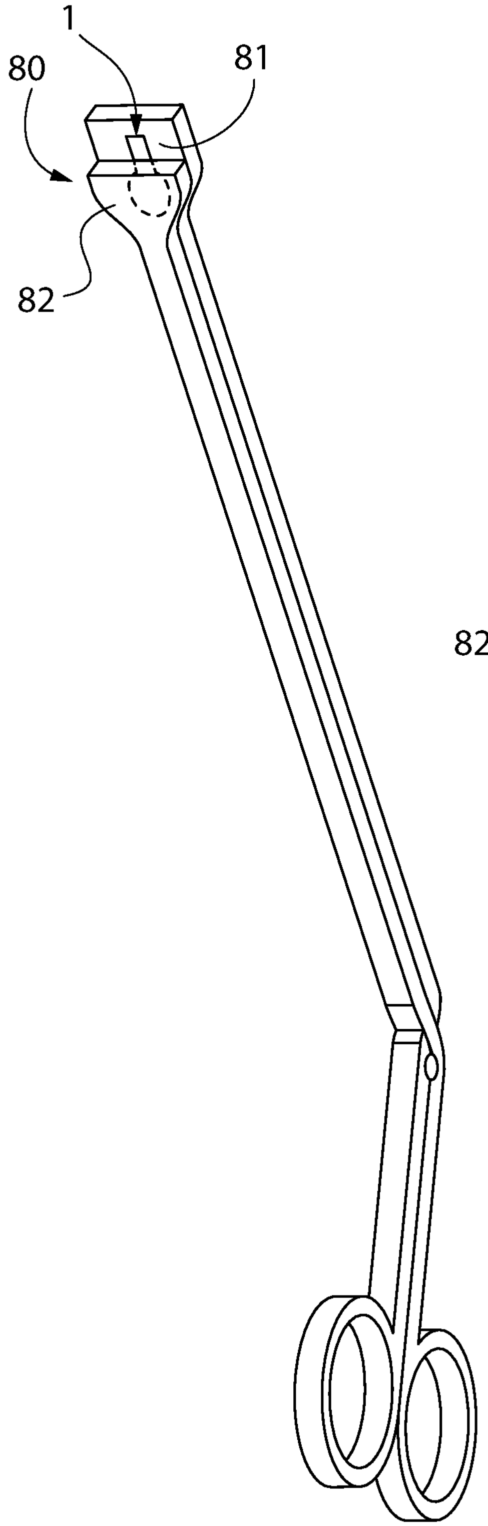
FIG. 17 is an implantation device for implanting a device as described herein, the implantation device in a first state.
Figure 18:
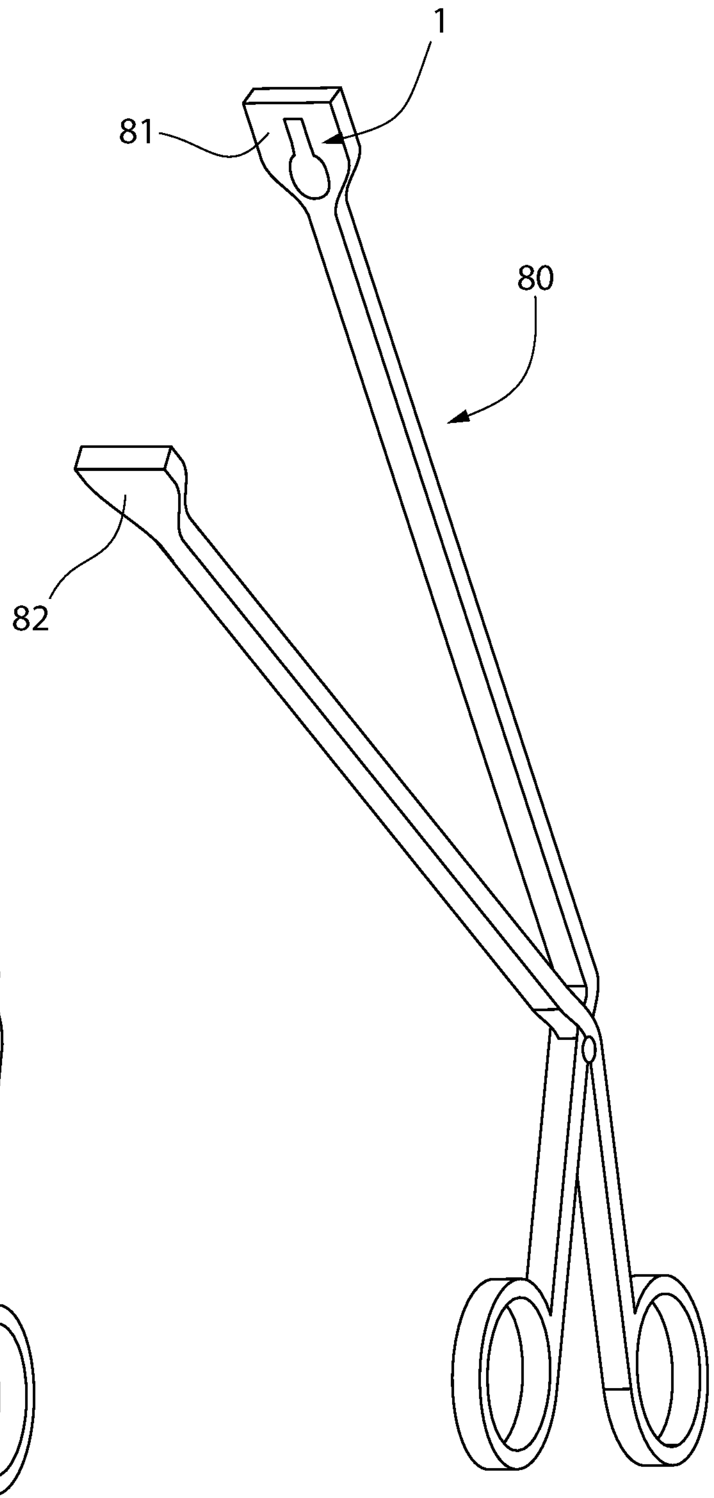
FIG. 18 is an implantation device for implanting a device as described herein, the implantation device in a second state.

Referring now to FIGS. 17 and 18—embodiments further comprise implantation device 80, implantation device 80 can be configured to implant treatment device 1 into eye 900. The following discussion will be made in reference to treatment device 1 but also applies to treatment device 1001, 2001, 3001, 4001.

According to this embodiment, a support scaffold may be used in combination with treatment device 1. Specifically, treatment device 1 may be placed atop a support scaffold, and together, the treatment device and support scaffold can be grasped by an implantation tool comprising first support 81 and second support 82. In a non-limiting embodiment, implantation device 80 may be forceps. As demonstrated by FIG. 17, in a first state, first and second supports 81, 82 pinch treatment device 1 and scaffold.

During implantation, an opening may be made to sclera tissue 913 on eye 900. Implantation device 80 in the first state may then be inserted into the opening such that first and second supports 81, 82 are positioned within the opening. Implantation device 80 may then be converted to a second state (as shown in FIG. 18), whereby first and second supports 81, 82 are separated, thereby freeing treatment device 1. Implantation device 80 may be converted from the first state to the second state manually by hand or with the aid of a machine.

Once in the second state, treatment device 1 can be transferred from first support 81 to eye 900. In one embodiment, both treatment device 1 and the support scaffold can be transferred to the eye, and once in proper position, the support scaffold can then be removed leaving only the treatment device in its final implantation position. In another embodiment, the treatment device 1 may be transferred to the eye without the support scaffolding, which remains on first support 81. The transfer of the treatment device 1 may occur by moving implantation device 80 (such as a slight oscillating movement), to force treatment device 1 from first support 81.

Figure 19:
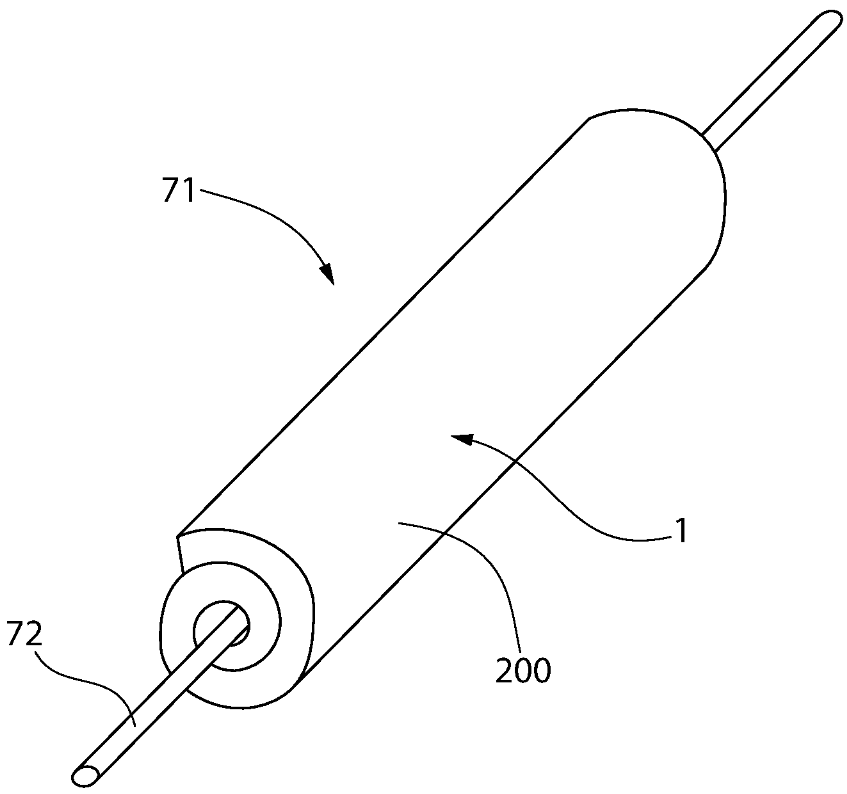
FIGS. 19-20 is an implantation device for implanting a device according to another embodiment.
Figure 20:
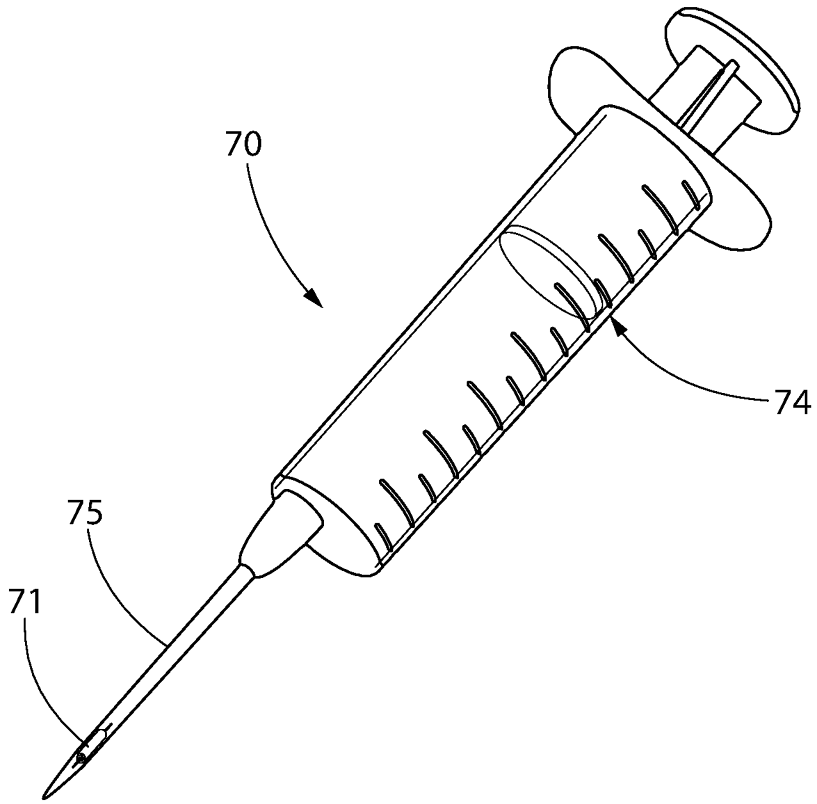
Figure 21:
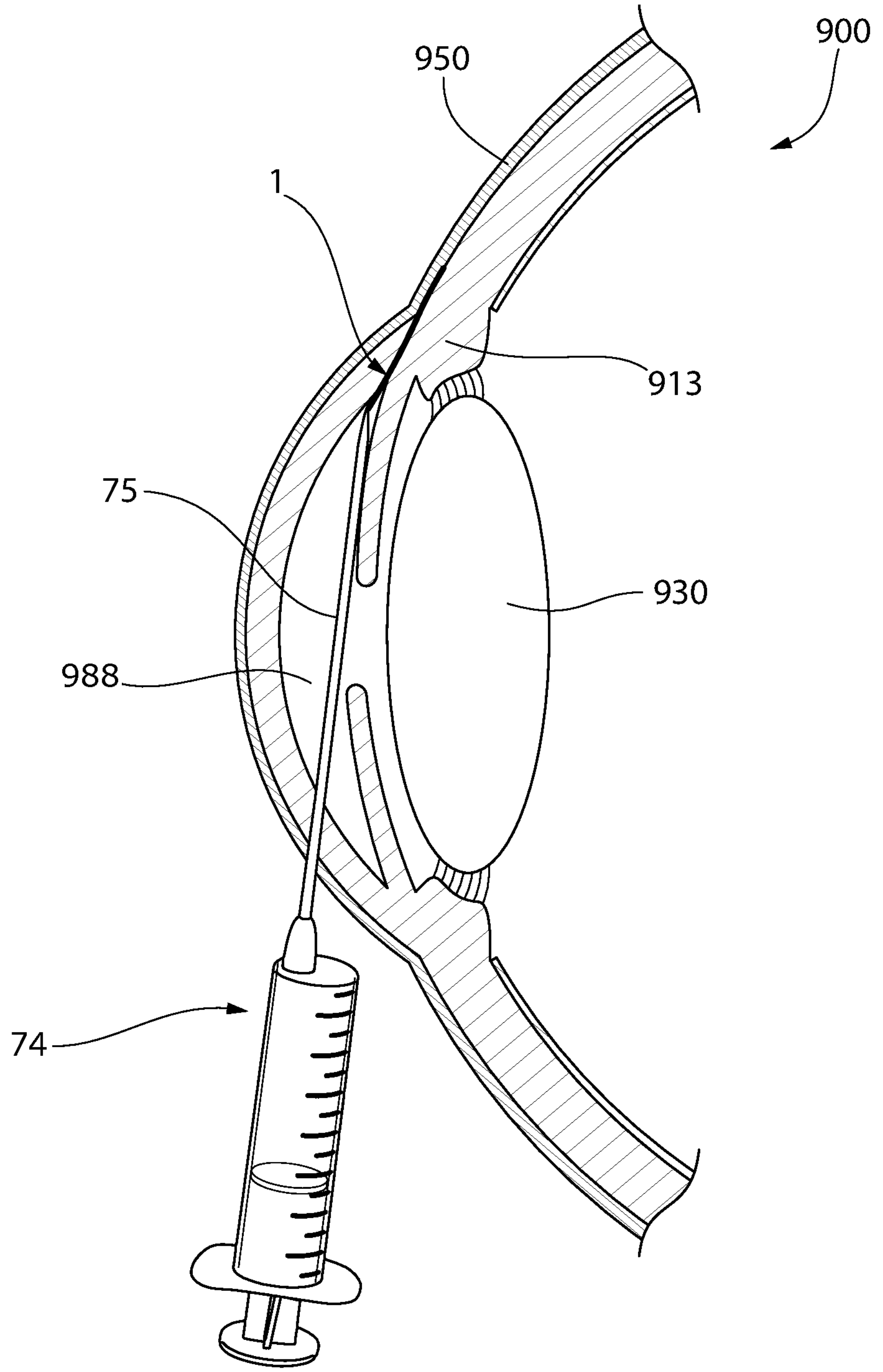
FIG. 21 is a close-up cross-sectional view of an eye being implanted with a device as described herein using the implantation device of FIGS. 19-20.

Referring now to FIGS. 19-21—embodiments further comprise implantation device 70, implantation device 80 configured to implant treatment device 1 into eye 900. The following discussion will be made in reference to treatment device 1 but also applies to treatment devices 1001, 2001, 3001, 4001.

According to this embodiment, the device described herein may further comprise injectable treatment device 71 comprising support rod 72 that is used in combination with treatment device 1. Specifically, treatment device 1 may be rolled about support rod 72 thereby forming an elongated columnar shape. In other embodiments, injectable treatment device 71 may not comprise support rod 72 and instead treatment device 1 may be rolled onto itself.

Injectable treatment device 71 may then be placed in injection apparatus 74 configured to inject injectable treatment device 71 into eye 900 via fluid pathway 75. In a non-limiting example, injection apparatus 74 may be a syringe and fluid pathway 75 may be formed by a needle.

During implantation, fluid pathway 75 may enter the bottom portion of anterior chamber 988 and extend upwards toward sclera 913, whereby treatment device 1 may be expelled from implantation device 70 by a pumping mechanism and delivered to sclera 913. Once delivered, treatment device 1 may unfurl from the rolled position about support rod 72, thereby creating a fluid pathway from anterior chamber 988 to a location between the conjunctiva and sclera 913 for excess aqueous humor to escape from anterior chamber 988.

Figure 22:
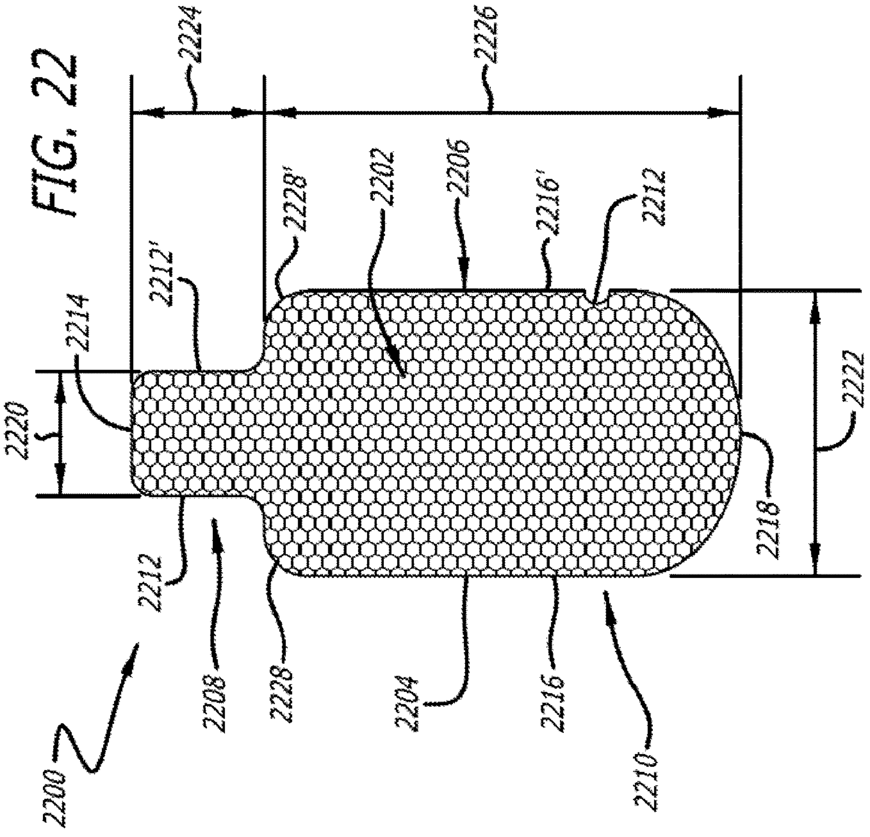
FIG. 22 illustrates an embodiment of a device as described herein.

In one embodiment, a device as described herein is illustrated in FIG. 22. Device 2200 includes plate structure 2202 having a first major exposed surface 2204 opposite a second major exposed surface (not illustrated) as well as a side surface 2206 extending there-between. The plate structure 2202 comprises an extension portion 2208 and a main body portion 2210.

In general, in FIG. 22, extension portion 2208 includes two substantially parallel side surfaces 2212, 2212' flanking a substantially flat end surface 2214. This portion can be referred to as the wick or neck. In this embodiment, the junctions of parallel side surfaces 2212, 2212' and substantially flat end surface 2214 are rounded. These rounded corners can have a radius of between about 0.2 mm and about 0.8 mm, between about 0.3 mm and about 0.8 mm, between about 0.4 mm and about 0.8 mm, between about 0.5 mm and about 0.8 mm, between about 0.6 mm and about 0.8 mm, between about 0.7 mm and about 0.8 mm, between about 0.4 mm and about 0.6 mm, or about 0.3 mm and about 0.7 mm. However, in other embodiments, these junctions need not be rounded.

Likewise, main body portion 2210 includes two substantially parallel side surfaces 2216, 2216.' These parallel side surfaces are flanked by a substantially rounded end surface 2218. In other embodiments, substantially rounded end surface 2218 can be a substantially flat end surface with rounded or un-rounded junctions.

Distance 2220 between two substantially parallel side surfaces 2212, 2212' is less than distance 2222 between substantially parallel side surfaces 2216, 2216.' In some embodiments, distance 2220 is between about 1 mm and about 10 mm, between about 1 mm and about 9 mm, between about 1 mm and about 8 mm, between about 1 mm and about 6 mm, between about 2 mm and about 6 mm, between about 3 mm and about 6 mm, between about 3 and about 7 mm, between about 3 and about 8 mm, or between about 4 and about 6 mm. In some embodiments, distance 2222 is between about 5 mm and about 10 mm, between about 5 mm and about 9 mm, between about 5 mm and about 8 mm, between about 5 mm and about 7 mm, or between about 5 mm and about 6 mm. In some embodiments, substantially rounded end surface 2218 can have a radius of between about 1 mm and about 5 mm, between about 1 mm and about 4 mm, between about 1 mm and about 3 mm, or between about 1 mm and about 2 mm.

Distance 2224 between substantially flat end surface 2214 and interface of extension portion 2208 and main body portion 2210 is between about 1 mm and about 5 mm, between about 1 mm and about 4 mm, between about 1 mm and about 3 mm, or between about 1 mm and about 2 mm. Distance 2226 between interface of extension portion 2208 and main body portion 2210 and substantially rounded end surface 2218 is between about 5 mm and about 15 mm, between about 5 mm and about 14 mm, between about 5 mm and about 13 mm, between about 5 mm and about 12 mm, between about 5 mm and about 10 mm, between about 5 mm and about 9 mm, between about 6 mm and about 15 mm, between about 7 mm and about 15 mm, between about 8 mm and about 15 mm, between about 9 mm and about 15, between about 10 mm and about 15 mm, or between about 9 mm and about 11.

Further, main body portion 2210 includes two substantially rounded corners 2228, 2228' at the interface of extension portion 2208 and main body portion 2210. However, these corners need not be rounded. In some embodiments, substantially rounded corners 2228, 2228' can have a radius of between about 0.2 mm and about 1 mm, between about 0.3 mm and about 1 mm, between about 0.4 mm and about 1 mm, between about 0.5 mm and about 1 mm, between about 0.6 mm and about 1 mm, between about 0.7 mm and about 1 mm, between about 0.8 mm and about 1 mm, or about 0.9 mm and about 1 mm. Further, the interface of extension portion 2208 and main body portion 2210 is curved. However, this portion need not be curved. The curvature can have a radius of between about 0.2 mm and about 0.8 mm, between about 0.3 mm and about 0.8 mm, between about 0.4 mm and about 0.8 mm, between about 0.5 mm and about 0.8 mm, between about 0.6 mm and about 0.8 mm, between about 0.7 mm and about 0.8 mm, between about 0.4 mm and about 0.6 mm, or between about 0.3 mm and about 0.7 mm.

In some embodiments, device 2200 can include an indicium indentation 2212. Indicium indentation 2212 can be located anywhere on the periphery of side surface 2206 on either extension portion 2208 or main body portion 2210.

In some embodiments, device 2200 can include two or more indicium indentations.

Indicium indentation(s) can have virtually any shape. Shapes can include curved shapes, rectilinear shapes and the like. In one embodiment, as illustrated in FIG. 22, indicium indentation 2212 has a shape of a semicircle. However, indicium indentation 2212 could have been a rectilinear shape such as a pyramid or point.

Indicium indentation(s) can be present to assist proper orientation during implantation. In some embodiments, having a single indicium indentation can provide an implanter with a visual indication that the proper side of a device is facing up.

Figure 23:
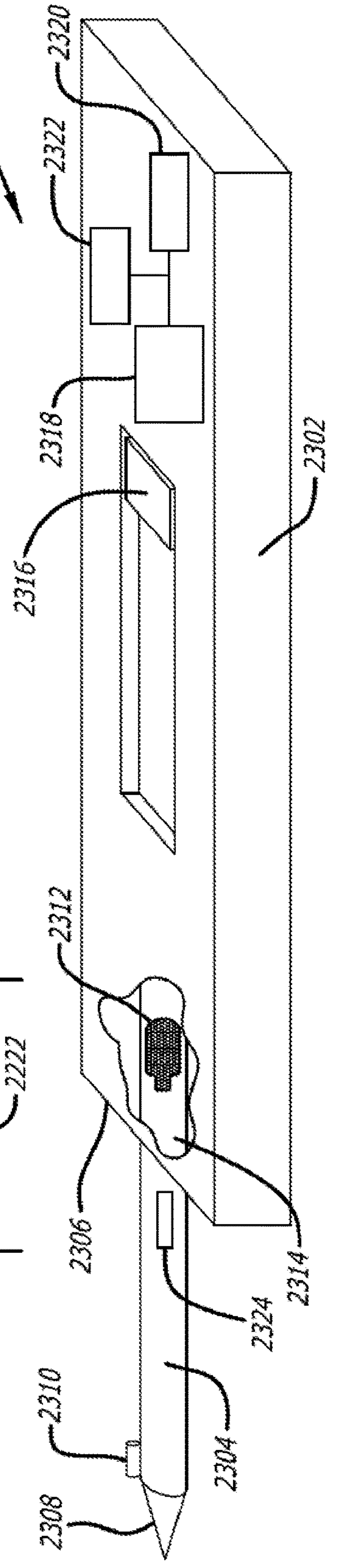
FIG. 23 illustrates an embodiment of an inserter or insertion device as described herein.

FIG. 23 illustrates a non-limiting embodiment of an inserter used to implant a device as described herein. Inserter 2300 includes a body or housing 2302. Housing includes a needle 2304 staked to its proximal end 2306. Needle 2304 has a sharp proximal end 2308. Sharp proximal end 2308 is used to puncture ocular tissues during device implantation. In some embodiments, needle 2304 is a low gauge needle such as a 40 gauge, 39 gauge, 38 gauge, 37 gauge, 36 gauge, 35 gauge, 34 gauge, 33 gauge, 32 gauge, 31 gauge, 30 gauge, 29 gauge, 28 gauge, 27 gauge, 26 gauge, 25 gauge, 24 gauge, 23 gauge, 22 gauge, 21 gauge, or 20 gauge needle.

Included on needle 2304 is a camera 2310. Camera 2310 is used to visualize the implantation process, and it can be a wired or wireless camera.

Device 2312 is housed within a compartment 2314 within housing 2302 near its proximal end 2306. However, in other embodiments, device 2312 can be housed within needle 2304.

A slider 2316 can be located on housing. Although slider 2316 is illustrated on the top of housing, it can be located on virtually any location of housing. The shape of slider is also shown for illustration purposes and can be virtually any shape that can be slid. Further, a mechanical slider may not be necessary. In some embodiments, slider 2316 can be replaced with a button and an electronic slide mechanism (not illustrated).

Circuit board 2318 can include a memory and a processor(s) for executing programs stored in the memory. For example, if a button is used instead of a slider, circuit board can effectuate that function. Circuit board 2318 is powered by battery 2320. Battery 2318 can be any battery that can power inserter 2300. Batteries can include, but are not limited to round, cylindrical batteries such as AA, AAA, AAAA, C, D, and button cell (such as lithium button), coin cell, and non-round batteries such as 4.5V box and 9V box batteries, and the like. Further button cell or coin cell batteries can be used. Batteries can be removed as needed. In some embodiments, the battery can be rechargeable.

Wireless interface 2322 is further associated with circuit board 2318. This interface can be any wireless interface type such as WiFi, Bluetooth, cellular, or the like. This interface can transmit camera data, device data, or the like.

In some embodiments, inserter 2300 is disposable. In other embodiments, inserter 2300 can be a multi-use device that can be cleaned and sterilized between uses.

During use, a device 2312 is loaded into compartment 2314. In some embodiments, device 2312 comes preloaded in the inserter. As the slider is moved, device is extruded from sharp proximal end 2308 of needle 2304. In some embodiments, a rolling device 2324 is located within compartment 2314 or needle 2304 that serves to roll the device as it is extruded. In other embodiments, the device is pre-rolled or rolled when loaded at the factory for a pre-loaded inserter.

In some embodiments, the herein described device can be used to enhance glaucoma treatment even when using other devices and methods. The device can be inserted prior to or after the insertion of another ocular device, such as a stent. The device can be used along with another glaucoma stent with the current device acting as a tissue separator for the ocular tissues. This separation of tissues can enhance the performance of an ocular stent for the treatment of glaucoma.

In some embodiments, the current device can be used as a substitute for Mitomycin C injections following eye surgeries. In some embodiments, the device is inserted in the eye during surgery. In other embodiments, the device is inserted after the surgery in a subsequent procedure. The device can aid in reducing the intraocular pressure associated with the surgery.

Example 1

A study is conducted to assess the herein described device's ability to decrease eye pressure and protect the optic nerve. Devices are implanted to determine if aqueous humor flows in a slow and controlled way through networked microchannels in a device to the subconjunctival space, forming a low and diffuse bleb.

| Experimental Design | |
|---|---|
| Species | *Oryctolagus cuniculus* |
| Strain | New Zealand White rabbits |
| Sex | Male or female (all same sex) |
| Age | Commensurate with weight |
| Weight | Approximately 2.5 to 3.0 kilograms at study start |
| Number | 3 (+ up to 3 extras) |
| Caging | As per ASC SOPs |
| Minimum Acclimation | 5 Days |

Test articles are provided as parylene-alumina composite material manufactured via atomic layer deposition and chemical vapor deposition as described herein. The articles are stored a room temperature and standard atmospheric pressure.

Prior to placement on study, each animal will undergo an ophthalmic examination (slit-lamp biomicroscopy and indirect ophthalmoscopy) by the Study Director or the Principal Investigator. Ocular findings will be scored according to a modified McDonald-Shadduck Scoring System. The acceptance criteria for placement on study will be scores of "0" for all variables.

Prior to placement on study, each animal is acclimated to the intraocular pressure (IOP) measurement procedures once daily for 5-7 days prior to study initiation to habituate the animals to the IOP procedure and to determine baseline IOP levels. IOP measurements are performed with a Tonovet rebound tonometer at the same times of day (±1 hour) as the IOP measurements. At least three measurements are taken per eye per each measurement event.

Animals are anesthetized with intramuscular (IM) injections of ketamine hydrochloride (up to about 50 mg/kg) and xylazine (up to about 10 mg/kg) or dexmedetomidine (about 0.25 mg/kg). Glycopyrrolate (about 0.01 mg/kg, IM) may be administered concurrently. Atipamezole hydrochloride (up to 1 mg/kg) may be used as a reversal agent.

After surgical preparation of eyes, one to two drops of topical proparacaine hydrochloride anesthetic (0.5%) are applied to the animal's eyes. Additional topical ocular anesthesia dosing may be utilized during the procedures if needed.

The test article is implanted into the subconjunctival space of the right eye (OD) on Day 0.

The eyes are cleaned with Betadine and then rinsed with balanced salt solution (BSS). One to two drops of topical proparacaine hydrochloride anesthetic (0.5%) are applied to the animal's eyes. Additional topical ocular anesthesia dosing may be utilized during the procedures if needed. The eye may be draped and a sterile wire speculum may be placed to retract the eyelids.

A 60 to 90-degree fornix based conjunctival peritomy is made in the superiortemporal quadrant, with the initial conjunctival incision made 2 mm posterior to the limbus. The length of the pocket should be 8 mm from the initial incision.

A stab incision into the anterior chamber is made 1 mm from the limbus with a keratome blade to create a scleral tunnel between the subconjunctival pocket and the anterior chamber.

The test article is gently grasped using forceps. Care is taken when handling the test article, as the material is very delicate and may stick to wet surfaces. The implant is inserted gently into the subconjunctival pocket.

Care is taken that the implant is inserted with the rounded notch located on the left-hand side to ensure the proper orientation of the implant with the channels on the top. The neck of the implant is gently guided into the scleral tunnel to confirm ease of entry. The body of the implant may be gently smoothed out to ensure it is properly positioned and lying flat. BSS will be used to moisten the tissues as needed.

If anterior chamber collapses or globe hypotony is present, then a 27-gauge needle and 3 mL syringe is used to inflate the anterior chamber with BSS. Inflating the AC with viscoelastic may make it difficult for neck of the implant to stay in AC, but viscoelastic can be used for lubricating the implant.

The implant is anchored to the sclera using 10-0 nylon or prolene sutures by passing the suture through the device at each of the corners and the tail.

The conjunctiva is closed with 10.0 nylon sutures or similar to create a watertight closure using a simple continuous pattern, avoiding the implant body as much as possible.

If the test article is difficult to see, a felt-tip surgical marker may be used to mark the bulbous body portion of the implant.

Animals are recovered immediately after test article administration and monitored during recovery until the animals are fully recovered.

One injection of buprenorphine (0.02-0.05 mg/kg IM/SC) is given perioperatively for analgesia. Additional buprenorphine administrations are given twice daily (about 12 hours apart) on Days 1 through 3 after test article administration. Alternatively, sustained-release buprenorphine (about 0.1 mg/kg SC) may be administered on Day 1.

One drop of 0.3% ofloxacin and one drop of 1% prednisolone acetate are applied on Day 0 after completion the implantation procedure and then 4× daily on Days 1 through 7 after test article administration.

Clinical ophthalmic examinations (slit-lamp biomicroscopy only) are performed on both eyes (OU) of all study animals at baseline (prior to test article administration), on Day 0 immediately after test article implantation, and on Days 1, 3, 7(±1), 14(±1), and 21(±3). In the case of optional study extension, additional examinations will be performed on Days 35(±3), 49(±3), 63(±3), 77(±3), & 91(±3).

Intraocular pressure (IOP) measurements are performed on both eyes (OU) of all study animals at baseline (prior to test article administration), on Day 0 immediately after test article implantation, and on Days 1, 3, 7(±1), 14(±1), and 21(±3). In the case of optional study extension, additional TOP measurements are performed on Days 35(±3), 49(±3), 63(±3), 77(±3), & 91(±3).

TOP measurements are performed with a Tonovet rebound tonometer at the same time each day (±1 hour) by the same technicians. At least three measurements are taken per eye per each measurement event.

Slit-lamp photographs are taken of both eyes (OU) of all study animals at baseline (prior to test article administration), on Day 0 immediately after test article implantation, and on Days 1, 7(±1), and 21(±3).

Fluorescein testing to evaluate the patency of the test article and the passage of aqueous humor from the anterior chamber to the subconjunctival space are performed in all right eyes (OD) on Day 21(±3).

The anterior chamber is entered with a small (about 30 gauge) needle and aqueous humor is allowed to drain from the anterior chamber to avoid excessive intraocular pressure (IOP). A second small needle is introduced into the anterior chamber and about 0.5 mL of a 0.01% sodium fluorescein solution in balanced salt solution (BSS) will be slowly infused into the anterior chamber over 20 minutes. TOP will be monitored during the procedure to ensure safe levels are not exceeded.

Observations after injection will be recorded in the raw data, including notes on passage (or lack thereof) of fluorescein into the test article and into the subconjunctival space.

Digital photographs of the eye may be taken using a slit-lamp or DSLR camera as needed to document the findings. Additional photographs may be taken using a fluorescein filter and/or a cobalt blue filter.

Figure 24:
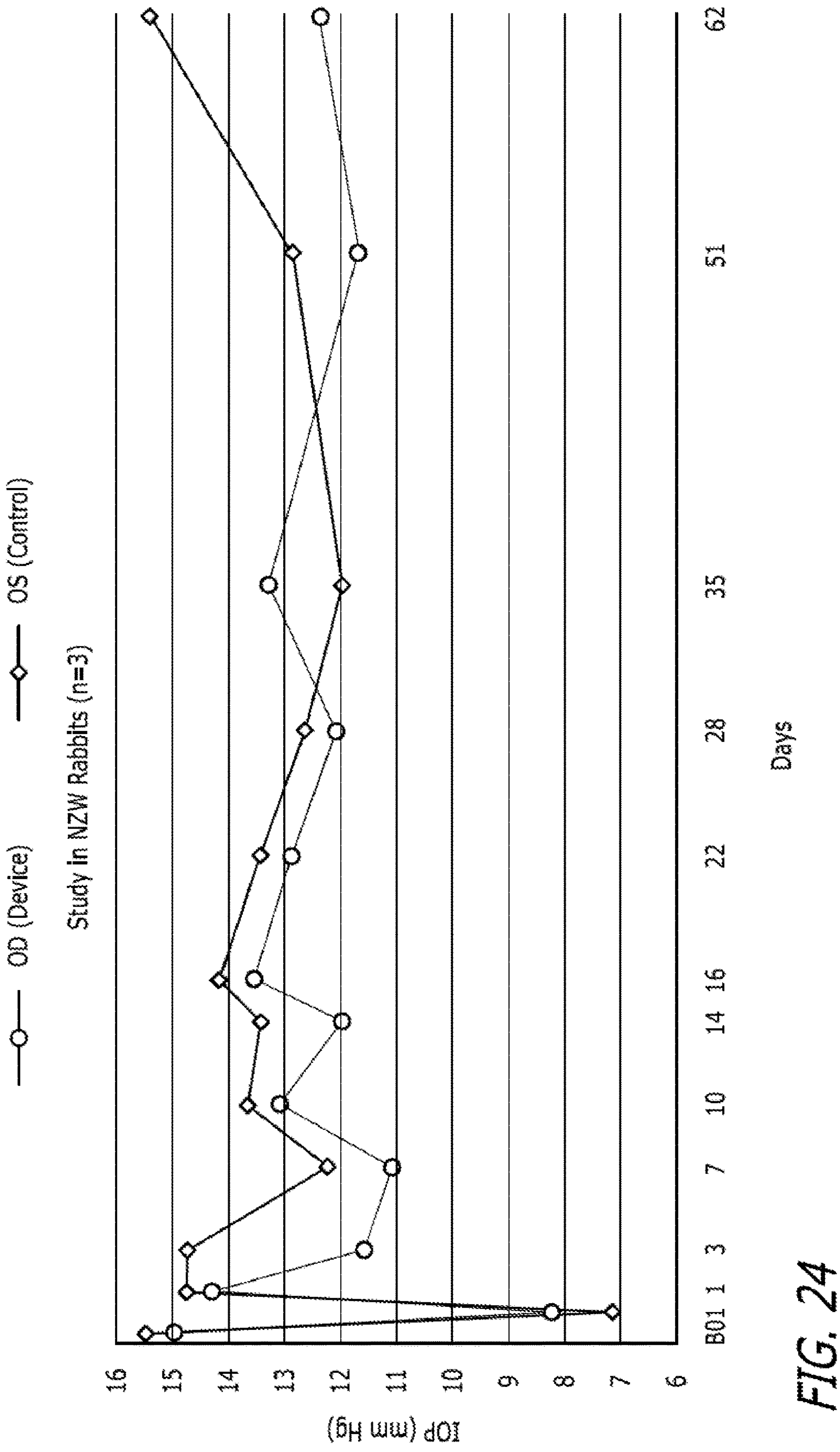
FIG. 24 illustrates intraocular pressure after insertion of a device as described herein.

As illustrated in FIG. 24, intraocular pressures in the treated eyes decreased an average of 25% from baseline on Day 7, and remained lower than baseline and control. The baseline score is an average of 5 days' intraocular pressure before the operation to implant the devices.

Blebs are present over all the implants.

Further, low scores occur for all ocular observations according to the McDonald-Shadduck Scoring System.

Example 2

Figure 25:
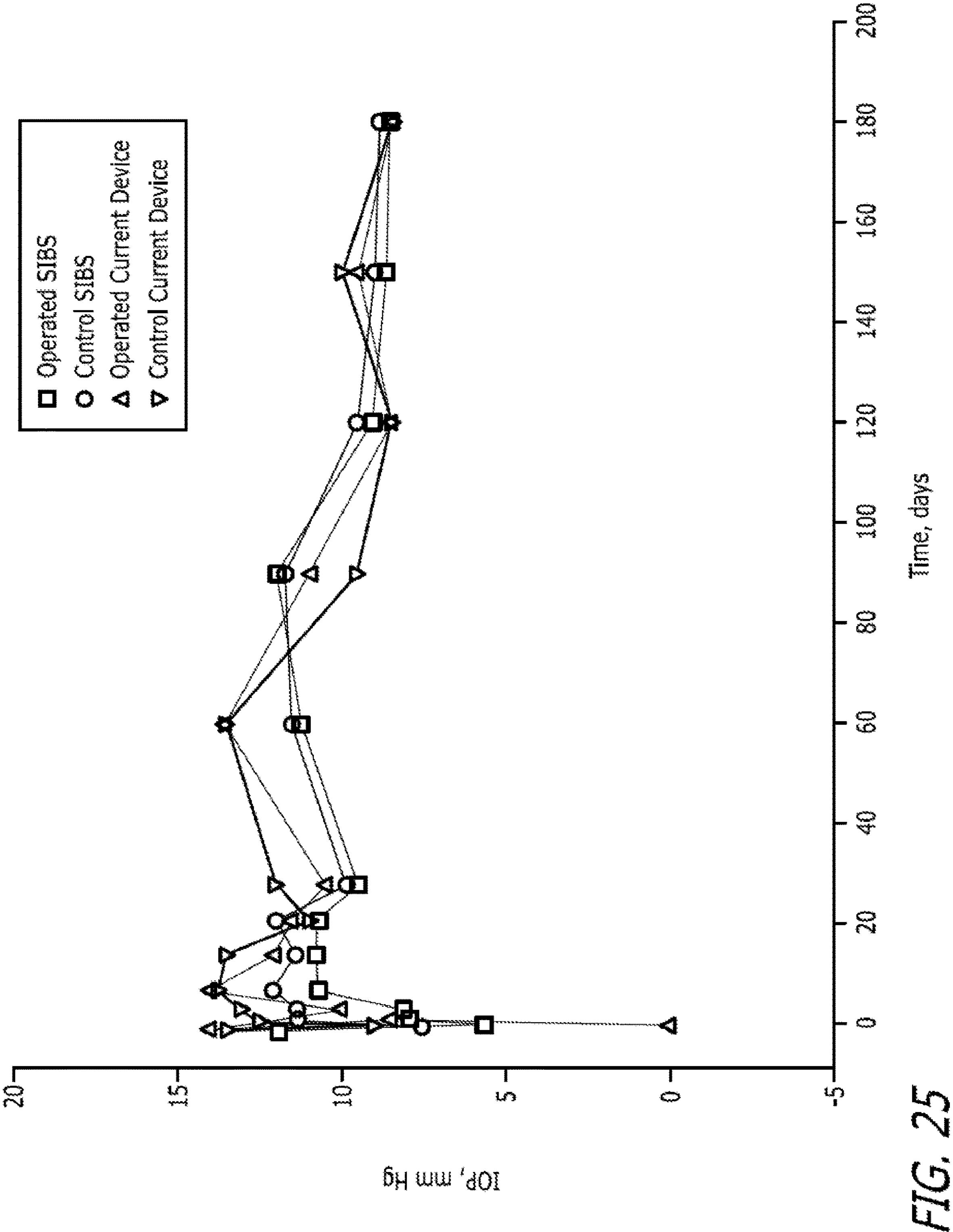
FIG. 25 illustrates intraocular pressure comparison between the devices described herein and SIBS devices.

The results of the Example 1 Study are compared to results using an InnFocus SIBS device. As illustrated in FIG. 25, intraocular pressures are lower in test eyes using the currently described devices than control for 22 days post-op.

Conversely, no statistically significant difference in intraocular pressure reduction is observed between eyes implanted with a SIBS implant and control eyes 7 days post-op.

Example 3

The Example 1 cohort is used for further study. On Day 22, 0.5 mL of 0.01% sodium fluorescein is injected over 20 minutes into the anterior chamber. Fluorescein dye flows into the subconjunctival bleb created by the current devices, indicating channel patency. Further, a large, diffuse filtration zone is maintained beyond the device surface area and beyond the dissection zone thereby illustrating flow out of the anterior chamber.

Example 4

Single or multiple layer plate(s) are implanted in the subconjunctival space via an ab-interno and minimally-invasive approach using an Insertion device such as, but not limited to a gel stent. A small portion of the Device (few mm in length) lies in the anterior chamber, allowing aqueous humor to flow along it into the subconjunctival space (between the tenon's capsule and sclera) via capillary action.

Fluid flow is through microchannels in plate and above/below the plate. Orientation of microchannels can be facing either the conjunctiva or sclera to maximize flow.

The device is pre-loaded into a capsule or cartridge that fits into an insertion device. The insertion device facilitates deposition in the correct position in the eye and then is withdrawn from the eye while the device remains.

The insertion device has a tapered, flat/rectangular blade that will make the minimally invasive cut, starting from the cornea of the inferior nasal quadrant of the eye, moving upwards and pushing tissue aside in the superior temporal quadrant. The blade can be tapered or can open up to prevent tissue from clogging the opening and preventing plate from being deposited. The tip of the insertion device, or the body of the blade of the insertion device has a ridge that stops it from cutting too deeply into the tissue. The ridge further helps with positioning of the blade and cutting using it.

Once the blade has opened an outflow pathway from the anterior chamber to the subconjunctival space, the insertion device will push the device, either through the blade or deposited via some system, into the open space, depositing it just so that the majority of the plate is in the tissue but a few mm extend into the anterior chamber. The insertion device is then removed and the surgeon closes any openings left in the eye.

Example 5

This Example illustrates the use of a device to lower intraocular pressure and the tolerability of the device when implanted beneath the conjunctiva in New Zealand White Rabbits.

Surgical Methods:

Three experimentally naive New Zealand White rabbits (1 male and 2 females), approximately 5 months old and weighing 2.8 to 3.3 kilograms for males and females at the outset of the study are assigned to treatment groups as shown in Table 1 below.

TABLE 1

| | | | Number of Animals | |
|---|---|---|---|---|
| Group | Left eye | Right Eye | Male 1 | Female 2 |
| Test Article | Insertion between the sclera and the conjunctiva via a conjunctival incision | Sham incision in the conjunctiva | | |

To implant the treatment device, each rabbit is anesthetized with a combination of Ketamine (40 mg/kg) and Xylazine (4 mg/kg) subcutaneously. Anesthetics are supplemented as needed. All drug usage is documented in the raw data. A few drops of 1% proparacaine (topical anesthesia) are placed in each eye at this time as well. Once anesthetized, the rabbit is placed in lateral recumbency and the area surrounding the eye prepped with a Swapstick containing 10% Providone-iodine. The eye is then rinsed with 0.9% sterile saline and another few drops of proparacaine given. A sterile drape is placed over the rabbit allowing exposure of the eye. Sterile instruments (steam autoclaved prior to first procedure and then chemically sterilized in chlorhexidine solution and rinsed with sterile water/saline between animals). Sterile gloves are worn.

The eyelid is kept open manually or with an eyelid speculum for the procedure. The eye is rotated medially using Colibri forceps and a small incision made in the conjunctiva lateral to the iris. A subconjunctival pocket is created ventrally and the treatment device placed within. Upon placement, the eye is allowed to rotate back to normal position and placement of the treatment device is observed to assure it is lying well within the subconjunctival pocket. The rabbit is then rotated to the other side and a sham procedure performed similarly on the contralateral eye, with no treatment device or other material implanted. Sterile ophthalmic ointment is placed on both eyes during the recovery period.

Observations mid Measurements:

The treatment device is implanted into the eye of the subjects on Day 1 via a conjunctival incision between the sclera and the conjunctiva. Mortality and clinical observations are evaluated daily. Ocular irritation scores are recorded prior to dose on Day 1, once daily on Days 2-5, Day 12, and Day 19. Body weights are recorded weekly. Food consumption is recorded daily. All animals are sacrificed on Day 21. The eyes with optic nerve for all animals are harvested at necropsy and evaluated microscopically.

Histological Analysis:

The animals are sacrificed with an overdose of an intravenous barbiturate on Day 21. All animals are necropsied. The eyes with optic nerve are collected and immediately fixed in Davidson's fixative for 24-48 hours. After the nerve specimens are dehydrated with increasing concentrations of ethanol (30-100%), the nerves are sectioned with a sharp razor blade. The sections are then embedded in paraffin in descending order and sectioned at 3 mm in thickness. The sections are stained with hematoxylin and eosin. Two sections (halves of the globe) with pupillary-optic disc orientation are trimmed from each eye, and two levels are microtomed per paraffin block, resulting in four slides per eye available for microphonic examination, Results and Discussion One male and two females New Zealand White rabbits are dosed once on Day 1 with the treatment device via a conjunctival incision between the sclera and the conjunctiva.

Mortality/Morbidity: There are no early deaths during the study. All animals survived until their scheduled sacrifice on Day 21.

Clinical Observations: On Day 1, mild to moderately decreased behavioral activity is noted post-surgery, and all animals have closed or partially closed eyes at 2-4 hours post-dose. These findings are considered test article unrelated and are secondary to the anesthesia and surgical procedures. All animals appear normal on study days 2-21.

Ocular Observations: The eyes of all animals (left and right) have ocular Draize scores of 0 prior to dosing on Day 1. Minimal overall Draize scores are recorded on study Days 2 and 3. Scores are noted in both, the left and right eye (drainage device implant and sham procedure, respectively). By Day 4, no ocular scores are noted. Table 2 below, summarizes the overall ocular Draize scores recorded during the study.

TABLE 2

| | Overall Ocular Draize Score | | | | | |
|---|---|---|---|---|---|---|
| | Left Eye Animal # | | | Left Eye Animal # | | |
| Day | 1 | 2 | 3 | 1 | 2 | 3 |
| 1 | 0 | 0 | 0 | 0 | 0 | 0 |
| 2 | 0 | 2 | 2 | 0 | 2 | 0 |
| 3 | 0 | 2 | 2 | 0 | 0 | 2 |
| 4 | 0 | 0 | 0 | 0 | 0 | 0 |
| 5 | 0 | 0 | 0 | 0 | 0 | 0 |
| 12 | 0 | 0 | 0 | 0 | 0 | 0 |
| 19 | 0 | 0 | 0 | 0 | 0 | 0 |

Body weight: No apparent test article-related effects on body weight or body weight gains are noted.

Food consumption: There are no test article-related effects on food consumption. The animals eat all their food on essentially all days.

Postmortem Observations

Gross necropsy findings: No gross necropsy findings are noted at scheduled sacrifice on Day 21.

Histopathology: The treatment device is not visible microscopically in any animal. A focal scleral alteration is noted neat the limbus in several eyes, consisting of an elevation and separation of conjunctiva and superficial collagen fibers from the deeper collagen fibers of the sclera, creating an empty space. Aside from fragmentation of collagen, no notable tissue reaction is evident. While a defect of minimal (Grade 1) severity is noted in two control (right) eyes, defects of mild (Grade 2) to moderate (Grade 3) severity are evident in two out of three treated (left) eyes, rising suspicion that the tissue defects in the eyes receiving the treatment device could at least in part represent implant sites in which the implant fragmented or washed our during processing. Conjunctival hyperplasia, lymphoplasmacytic infiltrate, and/or fibrosis of minimal severity are noted near the limbus in right and left eyes of all three animals. These lesions can be explained as spontaneous background findings and/or associated with surgical manipulation.

In summary, no test related clinical observations, effects on body weight or body weight gains, or effects on food consumption are noted. Post-surgery, overall Draize scores are minimal and all eyes appeared normal by Day 4. No gross necropsy findings are noted at scheduled sacrifice on Day 21. The treatment device is not visible after tissue processing, and no tissue reaction is noted at the implant site. In conclusion, the treatment device when implanted beneath the conjunctiva in New Zealand White rabbits is well tolerated.

It will be understood that the foregoing only demonstrates the tolerability of a treatment device when implanted into the eye and is only illustrative of the principles of the present disclosure, and that various modifications can be made by those skilled in the art without departing from the scope and spirit of the present disclosure.

Example 6

Fibroblasts are cultured on the surface of plain plastic cell culture dishes, parylene-C coated patterned silicon wafers, and parylene-C coated cell culture dishes. The samples are left for 24 hours to attach on the surface at 37° C. Cell culture media is added and left to grow for 48 additional hours. Fibroblasts attached and grew normally on plain plastic dishes, but are floating in gross cell clumps and could not be counted on the parylene coated samples. These results demonstrate that parylene's hydrophobicity prevents adherence of fibrotic cells. Further, the results demonstrate that parylene can prevent tissue adhesion.

Example 7

Devices are described herein with parylene-C coatings are implanted in the subconjunctival space of NZW rabbits with communication to the anterior chamber. Implants and blebs are sectioned, fixed, and histologically examined after a period of 83 days.

The thickness of the fibrotic blebs of 3 rabbits are measured and results are in Table 3.

TABLE 3

| Animal | Location | Fibrosis thickness (μm) | Scleral Thickness (μm) | Conjunctival Thickness (μm) |
|---|---|---|---|---|
| 1 | OS | 0.269 | 104.73 | 222.40 |
| | OD | 0 | | |
| 2 | OS | 0.221 | 115.32 | 287.20 |
| | OD | 0 | | |
| 3 | OS | 0.247 | 75.30 | 227.40 |
| | OD | 0 | | |

Thickness of fibrosis is the average of four measurements: rostral, scleral, posterior and conjunctival. Thickness of fibrosis on the sclera and conjunctival sides are the average of four evenly spaced measurements on the respective side of the implant.

Results in Table 4 are also compared to implantation of the Ahmed Glaucoma valve in the same space, with and without amniotic membrane. The present devices show significantly lower fibrotic capsule thickness than the AGV.

TABLE 4

| | Roof (conjunctival thickness) | | | Floor (scleral thickness) | | |
|---|---|---|---|---|---|---|
| | Control | Study | p-value | Control | Study | p-value |
| Fibrous capsular thickness (μm) | 458 ± 60 | 280 ± 28 | <0.001 | 233 ± 43 | 227 ± 46 | 0.777 |
| Myofibroblast layer thickness (μm) | 304 ± 40 | 188 ± 26 | <0.001 | 75 ± 11 | 82 ± 10 | 0.168 |
| Blood vessel (n) | 7.03 ± 2.48 | 8.63 ± 3.29 | 0.235 | 4.90 ± 2.34 | 4.80 ± 2.47 | 0.927 |
| Leukocytes (n) | 4.00 ± 1.65 | 15.10 ± 7.42 | 0.001 | 2.04 ± 1.63 | 1.67 ± 2.13 | 0.665 |

These results demonstrate that a hydrophobic coating such as parylene and/or a patterned surface such as that of the devise described decreases fibrotic growth and scarring.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific example embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Example embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A device for lowering intraocular pressure, the device comprising:

a plate having a first end and a second end, the plate comprising a first surface opposite a second surface, wherein the first surface includes a series of fluid channels configured in an intersecting grid pattern extending from the first end to the second end of the plate, the first end of the plate being configured for insertion into an anterior chamber of an eye, and the second end of the plate being configured for insertion into a subconjunctival space of the eye;

a first coating on the first surface that conforms to a topography of the series of fluid channels; and a second coating on the second surface.

2. The device according to claim 1, wherein the plate includes a core that has a thickness of about 50 nm to about 800 nm.

3. The device according to claim 1, wherein the plate is formed from a ceramic material.

4. The device according to claim 3, wherein the ceramic material is selected from the group consisting of alumina, silicon nitride, silica, hafnium oxide, titanium nitride, and titanium carbide.

5. The device according to claim 1, wherein the first coating has a thickness of about 0.1 μm to about 1 μm.

6. The device according to claim 1, wherein the first coating is a parylene polymer.

7. The device according to claim 6, wherein the parylene polymer is parylene C, parylene D, parylene N, a derivative thereof, or a combination thereof.

8. The device according to claim 1, wherein the first coating is a polymeric material selected from rubber, synthetic rubber, silicone polymers, parylene, thermoplastics, thermosets, polyolefins, polyisobutylene, acrylic polymers, ethylene-co-vinylacetate, polybutylmethacrylate, vinyl halide polymers, polyvinyl ethers, polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides, alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene, poly(ether-ether-ketone), poly lactides including PLA, PLGA, PLLA, derivatives thereof, or combinations thereof.

9. The device according to claim 1, wherein the second coating has a thickness of about 0.1 μm to about 1 μm.

10. The device according to claim 1, wherein the second coating is aluminum oxide or a parylene polymer.

11. The device according to claim 1, wherein the second coating includes aluminum oxide, rubber, synthetic rubber, silicone polymers, parylene, thermoplastics, thermosets, polyolefins, polyisobutylene, acrylic polymers, ethylene-co-vinylacetate, polybutylmethacrylate, vinyl halide polymers, polyvinyl ethers, polyvinylidene halides, polyacrylonitrile, polyvinyl ketones, polyvinyl aromatics, polyvinyl esters, acrylonitrile-styrene copolymers, ABS resins, ethylene-vinyl acetate copolymers, polyamides, alkyd resins, polycarbonates, polyoxymethylenes, polyimides, polyethers, epoxy resins, polyurethanes, rayon, cellulose, cellulose acetate, cellulose butyrate, cellulose acetate butyrate, cellophane, cellulose nitrate, cellulose propionate, cellulose ethers, carboxymethyl cellulose, polytetrafluororethylene, poly(ether-ether-ketone), poly lactides such as PLA, PLGA, PLLA, derivatives thereof, or combinations thereof.

12. The device of claim 1, wherein the series of fluid channels includes a plurality of open-ended channels interconnected to form an intersecting network of fluid pathways.

13. The device of claim 1, further including a drug.

14. A method of reducing intraocular pressure comprising:

injecting a device into an eye with high intraocular pressure, the device including a plate having a first end and a second end, the plate comprising a first surface opposite a second surface, wherein the first surface includes a series of fluid channels configured in an intersecting grid pattern extending from the first end to the second end of the plate, the first end of the plate being configured for insertion into an anterior chamber of the eye, and the second end of the plate being configured for insertion into a subconjunctival space of the eye, the plate further comprising a first coating on the first surface that conforms to a topography of the series of fluid channels and a second coating on the second surface; and treating the high intraocular pressure.

15. The method of claim 14, further comprising securing the device to the eye.

16. The method of claim 15, wherein the securing is to a sclera of the eye.

17. The method of claim 14, wherein at least a portion of the first surface of the plate faces a conjunctiva of the eye and at least a portion of the second surface faces a sclera of the eye.

18. The method of claim 17, wherein the device forms a fluid pathway that provides fluid communication between the anterior chamber of the eye and a device position.

19. The method of claim 18, wherein the fluid pathway comprises the series of fluid channels.

20. The method of claim 14, wherein treating the high intraocular pressure is a treatment for glaucoma.

* * * * *